United States Patent
Lorbeer et al.

(10) Patent No.: US 10,126,230 B2
(45) Date of Patent: Nov. 13, 2018

(54) DEVICE AND METHOD FOR EXAMINING SAMPLES IN A LIQUID

(71) Applicants: Laser Zentrum Hannover e. V., Hannover (DE); LaVision BioTec GmbH, Bielefeld (DE)

(72) Inventors: Raoul Amadeus Lorbeer, Magstadt (DE); Marko Heidrich, Tubingen (DE); Heiko Meyer, Isernhagen (DE); Heinrich Spiecker, Bielefeld (DE)

(73) Assignee: LAVISION BIOTEC GMBH, Bielefeld (DE)

( * ) Notice: Subject to any disclaimer, the term of this patent is extended or adjusted under 35 U.S.C. 154(b) by 525 days.

(21) Appl. No.: 14/895,107

(22) PCT Filed: Jun. 3, 2014

(86) PCT No.: PCT/EP2014/001482
§ 371 (c)(1),
(2) Date: Dec. 1, 2015

(87) PCT Pub. No.: WO2014/195005
PCT Pub. Date: Dec. 11, 2014

(65) Prior Publication Data
US 2016/0109357 A1   Apr. 21, 2016

(30) Foreign Application Priority Data
Jun. 3, 2013   (DE) .................. 10 2013 210 269

(51) Int. Cl.
*G01N 21/00* (2006.01)
*G01N 21/11* (2006.01)
(Continued)

(52) U.S. Cl.
CPC ............. *G01N 21/11* (2013.01); *G01N 21/03* (2013.01); *G01N 21/0303* (2013.01);
(Continued)

(58) Field of Classification Search
CPC ........ G01N 21/11; G01N 21/03; G01N 21/17; G01N 21/63; G01N 21/64; G02B 21/26; G02B 21/34
See application file for complete search history.

(56) References Cited

U.S. PATENT DOCUMENTS

| 2005/0157386 A1 | 7/2005 | Greenwald et al. |
| 2006/0116828 A1* | 6/2006 | Chen ............ G01N 24/08 702/22 |

FOREIGN PATENT DOCUMENTS

| EP | 1530073 | 11/2007 |
| WO | 2012080478 | 6/2012 |
| WO | 2014195005 | 12/2014 |

OTHER PUBLICATIONS

Huisken et al., Selective plane illumination microscopy techniques in developmental biology, Development, vol. 136, Issue 1, Jun. 2009, pp. 1963-1975.

(Continued)

*Primary Examiner* — Abdullahi Nur
(74) *Attorney, Agent, or Firm* — Kilpatrick Townsend & Stockton LLP

(57) ABSTRACT

The invention relates to a device for examining samples (1) in a liquid (5), comprising a movable shaft (2), to which the sample (1) is fastened, and a cuvette (4), wherein the device further comprises a bath (3), which surrounds the movable shaft (2), and wherein the bath (3) is fillable with the liquid (5), the movable shaft (2) is configured to receive the sample (1) at the upper side (24) thereof, the movable shaft (2) reaches into the cuvette (4) from below, wherein said cuvette is open at least toward the bottom and configured to be immersed into the liquid (5) in the bath (3) with the underside thereof, and, moreover, means are provided to generate a pressure difference between the interior of the cuvette (4) and the region outside of the cuvette (4) such that (Continued)

the fill level (21) of the liquid (5) in the cuvette (4) is adjustable.

Moreover, the invention relates to a method for examining samples (1) in a liquid (5).

26 Claims, 9 Drawing Sheets

(51) Int. Cl.
  *G01N 21/03* (2006.01)
  *G02B 21/26* (2006.01)
  *G02B 21/34* (2006.01)
  *G01N 21/17* (2006.01)
  *G01N 21/63* (2006.01)
  *G01N 21/64* (2006.01)
  *G01N 21/65* (2006.01)
  *G02B 21/33* (2006.01)

(52) U.S. Cl.
  CPC .............. *G01N 21/17* (2013.01); *G01N 21/63* (2013.01); *G02B 21/26* (2013.01); *G02B 21/34* (2013.01); *G01N 21/6458* (2013.01); *G01N 2021/0342* (2013.01); *G01N 2021/653* (2013.01); *G01N 2201/02* (2013.01); *G01N 2201/06113* (2013.01); *G02B 21/33* (2013.01)

(56) References Cited

OTHER PUBLICATIONS

Keller et al., Digital scanned laser light sheet fluorescence microscopy, Cold Spring Harb Protoc., vol. 2010, Issue 5, May 2010.

Keller et al., Quantitative in vivo imaging of entire embryos with Digital Scanned Laser Light Sheet Fluorescence Microscopy, Current Opinion in Neurobiology, vol. 18, Issue 6, Dec. 2008, pp. 624-632.

Lorbeer et al., Highly efficient 3D fluorescence microscopy with a scanning laser optical tomograph, Optics Express vol. 19, Issue 6, Mar. 14, 2011, pp. 5419-5430.

International Application No. PCT/EP2014/001482, International Preliminary Report on Patentability dated Dec. 17, 2015.

International Application No. PCT/EP2014/001482, International Search Report and Written Opinion dated Oct. 16, 2014.

Sharpe et al., Optical projection tomography as a tool for 3D microscopy and gene expression studies, Science, vol. 296, Issue 5567, Apr. 19, 2002, pp. 541-545.

\* cited by examiner

DEVICE AND METHOD FOR EXAMINING SAMPLES IN A LIQUID

CROSS-REFERENCE TO RELATED APPLICATIONS

This application is a U.S. national phase under 35 U.S.C. 371 of International Patent Application No. PCT/EP2014/001482, entitled "DEVICE AND METHOD FOR EXAMINING SAMPLES IN A LIQUID", filed Jun. 3, 2014, which claims the benefit of German Application No. 102013210269.0, filed Jun. 3, 2013 the entire contents and disclosures of which are incorporated herein by reference.

The invention relates to a device for examining samples in a liquid, comprising a movable shaft, to which the sample is fastened, and a cuvette. Moreover, the invention relates to the use of the device for examining samples and a method for carrying out examinations of samples.

The restricted penetration depth of light is one of the fundamental problems in the field of optical microscopy for samples from biology and medicine. Therefore, it is advantageous to record the samples from a plurality of directions, as in e.g. optical projection tomography (OPT) described by J. Sharpe et al. in "Optical Projection Tomography as a Tool for 3D Microscopy and Gene Express Studies", Science 296, 541-545 (2002), in order to improve the microscopic scanning of the sample volume. Moreover, light sheet fluorescence microscopy or single plane illumination microscopy (LSFM or SPIM) should be mentioned as a further microscopic method, in which an excitation volume with a planar extent is illuminated. The signal light, which is generally fluorescence light, is detected by means of a detection objective which is arranged perpendicular to the excitation surface. Here, the excitation surface is imaged on a camera. An overview of light sheet fluorescence microscopy can be gathered from the article "Selective plane illumination microscopy techniques in developmental biology" by J. Huisken and D. Stainier in Development 135, 1963-1975 (2009). A more developed variant, "digital scanned laser light sheet fluorescence microscopy" (DSLM) was described by P. Keller and E. Stelzer in "Quantitative in vivo imaging of entire embryos with Digital Scanned Laser Light Sheet Fluorescence Microscopy", Current Opinion in Neurobiology 2008, 18:624-632.

In optical tomography, in which projection images are recorded perpendicular to an axis of rotation about which the sample is rotated, the projection images can be recorded by means of a camera as pure transmission or fluorescence images or they can be acquired as scanning tomography images in the case of scanning laser optical tomography (SLOT). In the case of scanning laser optical tomography, a narrow laser beam is scanned sequentially over the sample and passes therethrough. In the volume of intersection between the laser beam and the sample, the latter is excited or the laser beam is absorbed or scattered. The absorption, scattering intensity and fluorescence measured variables are measured sequentially for each scanning point of the laser beam and rotational angle of the sample. The sample volume is imaged from the data obtained by means of tomographic reconstruction. The method and a device for carrying out the method can be gathered from WO 2012/080478 A1.

Further optical examination processes comprise conventional wide-field microscopy, transmission microscopy, confocal fluorescence microscopy, coherent anti-Stokes Raman scattering (CARS) or nonlinear microscopy such as e.g. two or three photon microscopy, microscopy using high harmonics generation (HHG), confocal theta microscopy, fluorescence lifetime imaging microscopy (FLIM), stimulated emission detection microscopy (STED), optical coherence tomography (OCT) or structured illumination microscopy (SIM). The sample can also be moved, more particularly rotated, when data is recorded in these methods. Further examination processes comprise x-ray microscopy, x-ray tomography, imaging ultrasound methods and digital holography.

In the aforementioned methods, the samples are a usually rotated about an axis which is oriented substantially vertically or lies parallel to gravity such that the sample does not deform during the rotation as this would make the reconstruction of a data record from the individual recordings more difficult.

The samples to be examined generally have a refractive index of between 1.3 and 1.6 and have an irregular surface at which light can be scattered. In order to improve the optical properties, the sample is examined in an immersion liquid, the refractive index of which is similar to that of the sample. To this end, the sample is introduced into a cuvette filled with a liquid. Samples are often embedded in agarose gel and examined in aqueous solutions and/or cleared using clarification methods and then examined in a liquid with an appropriate refractive index. One of the difficulties lies in holding the sample on a rotary shaft, which is introduced into the cuvette either from below or hanging from above. If the sample is fastened to the rotary shaft, this does not yet ensure that said sample rotates precisely about its own axis when the rotary shaft rotates. If the sample is situated eccentrically on the shaft, it alternately migrates to both sides in respect of the detection window during the rotation. The image to be recorded or the projection surface then needs to be enlarged. In the case of scanning microscopic methods and single plane illumination microscopy, the scanning length along the detection axis must also be enlarged in the process.

In general, the access to the sample within the cuvette proves to be difficult when the rotational shaft is arranged in the vertical direction and one or more accesses for excitation or detection beam paths are required in the horizontal direction.

A further difficulty lies in a rotation of the sample about the axis thereof that is sufficiently precise for microscopy. The sought-after concentricity should lie in a region of approximately 1 µm if the data should be calculated without the complicated correction. Precise concentricity can easily be ensured if the rotational shaft is immersed contactlessly into the cuvette from above, but this makes access to the sample more difficult.

US 2005/157386 A1 has disclosed a sample holder which comprises a shell with an optical window in the base. At the lower side thereof, the sample holder has a foil bag with immersion liquid, wherein the liquid is connected to the interior of the shell by way of an opening. A sample can be placed on the optical window and it is bathed in the immersion liquid. The holder is placed onto optics from above, wherein the foil bag filled with liquid fills the clear space between the optics and the window. The sample holder can be moved relative to the optics.

The device known from WO 2012/080478 A1 for carrying out scanning laser optical tomography (SLOT) comprises a light source, a sample holder and a detector. The light source is configured to illuminate the sample with a needle beam and scan the latter over the sample. The sample holder is rotatably arranged in a cuvette filled with an immersion liquid. The axis of rotation of the sample holder is oriented substantially vertically and both the light source and the detection optics are aligned horizontally.

A device for carrying out examinations by means of "optical projection tomography" (OPT) is known, for example, from EP 1 530 073 B1. The device comprises a light source, an objective and a cuvette situated in the beam path. The cuvette can be filled with an immersion liquid, into which a sample can be immersed from above. To this end, the sample is fastened to a shaft in a magnetically hanging manner, which shaft is both rotatable and displaceable along the three spatial directions. Both the cuvette and the optical components remain stationary during the examination such that the sample can move independently of the optical elements.

If—as in the devices known from the prior art—the sample is held from above and lowered into cuvette there is no need for sealing the cuvette in relation to the rotational shaft, but the access to the sample is made more difficult thereby. Moreover, the sample must be fastened so securely to the shaft that it does not fall off during the measurement. This is particularly difficult if this is an examination of living samples, such as in the case of embryo growth of e.g. zebrafish.

In many cases, particularly in the case of high-resolution methods, use is made of immersion objectives which are lowered into the cuvette from the side through an opening. To this end, a seal which enables focusing is necessary. In the process, frictional forces may occur, causing a reduced accuracy of the focusing, particularly if the focusing is brought about by means of piezo-actuators.

The required seals constitute a further problem since many of the conventionally used immersion liquids, and also the clearing media, are aggressive, and so the materials used for the seals may be attacked.

In the case of scanning tomography, it is moreover desirable for the optical components to be stationary and for only the sample to be rotated such that the fluorescence light collected by the detectors travels an identical path on the way out of the sample for each rotational angle. What this ensures is that the detection efficiency remains the same for each point during the rotation. This avoids artifacts in the reconstruction.

A further object of the invention is to provide a device which enables examinations of samples in a liquid, in which the samples can be moved during the examination, without seals which enable a movement during the examination being exposed to the immersion liquid. A further aspect of the invention lies in providing a corresponding method for carrying out optical examinations.

A device for examining samples in a liquid is proposed, comprising a movable shaft, to which the sample is fastened, and a cuvette, wherein the device furthermore comprises a bath, which surrounds the movable shaft, and wherein the bath is fillable with the liquid, the movable shaft is configured to receive the sample at the upper side thereof, the movable shaft reaches into the cuvette from below, wherein said cuvette is open at least toward the bottom and configured to be immersed into the liquid in the bath with the underside thereof, and, moreover, means are provided to generate a pressure difference between the interior of the cuvette and the region outside of the cuvette such that the fill level of the liquid in the cuvette is adjustable.

In one embodiment, the device is configured to enable optical examinations to be carried out on the sample. In particular, to this end, the cuvette is configured in such a way that at least parts of the wall thereof and/or the cover thereof are transparent to the radiation used during the optical examination. The term "optical examinations" means methods which during the examination irradiate the sample with electromagnetic radiation and/or evaluate electromagnetic radiation emitted by the sample. By way of example, the wavelength of the electromagnetic radiation lies between 300 nm and 2 μm.

In one embodiment of the device, the latter is configured to use an immersion liquid as liquid.

The movable shaft of the device is aligned substantially vertically, but it can also be inclined in relation to the vertical for adjustment purposes.

Here, the sample is affixed to the upper side of the movable shaft. This can be brought about, for example, by adhesive bonding, in particular by using an optically transparent adhesive, or by clamping. Skewering the sample onto a needle or a bed of needles is also conceivable. If the sample is held on a carrier or an intermediate piece, magnetic fastening or fastening by way of screws is also conceivable, depending on the embodiment. In one variant of the device, the shaft can have a depression at the upper side thereof, in which depression the sample can be held.

The bath of the device surrounds the movable shaft and it is filled with a liquid for carrying out the optical examination. If the liquid is an immersion liquid, the refractive index thereof is selected in such a way that it approximately corresponds to the refractive index of the sample. In this case, the fill level of the liquid or the immersion liquid in the bath lies below the level of the sample which is arranged at the upper end of the movable shaft. In order to surround the sample with the immersion liquid, a cuvette is lowered over the movable shaft in the direction of the base of the bath from above. The cuvette is a vessel which is at least open toward the bottom and preferably has straight walls. At least parts of the walls and, optionally, the cover of the cuvette are transparent to the employed radiation in the case of an optical examination such that the sample remains optically accessible. A gap remains between the bath base and the lower edge of the cuvette after lowering the cuvette such that the immersion liquid can flow through said gap and a connection remains between the interior of the cuvette and the region outside of the cuvette. A pressure difference is subsequently generated between the interior of the cuvette and the region outside of the cuvette. If the pressure within the cuvette is lower than the pressure in the region outside of the cuvette, the immersion liquid is pressed out of the bath and into the cuvette by the pressure difference and the fill level of the immersion liquid in the interior of the cuvette increases. As a result of a suitable selection of the pressure difference, it is possible to set the fill level of the immersion liquid within the cuvette. The optical examinations can be started once the sample is immersed in the immersion fluid. If the sample is intended to be moved in the process, this can be brought about by an appropriate movement of the movable shaft, which transmits this movement to the sample. Once the examination is completed, the pressure can be equalized again and the fill level of the immersion fluid in the interior of the cuvette can be lowered again as a result thereof.

In one embodiment of the device, the movable shaft is arranged in a rotatable manner. The axis about which the movable shaft is rotated preferably extends substantially vertically.

This renders it possible to carry out optical tomographic examinations using the device, during which the sample needs to be moved and, in particular, be examined from a plurality of directions. Depending on the embodiment of the device, the rotation of the sample is carried out by hand or an appropriate drive is arranged. If a drive is provided, it is moreover conceivable for the latter to be actuated in an automated manner, wherein provision can be made for a device such as e.g. a computer to control the progress of the optical examination.

In one embodiment of the device, the movable shaft is rigidly connected to the bath. Here, in one variant, the bath and the shaft are assembled from two parts, wherein a rigid connection is established e.g. by adhesive bonding, by a press fit, by way of a tongue and groove, by magnets, by screws or by welding. In a further variant, the bath and the movable shaft have an integral embodiment. In both cases, the bath and the shaft are moved together such that there is no need for a movable seal between the movable shaft and the bath. Here, the device with which the bath and the shaft are moved can be configured in such a way that the movable shaft can be removed together with the bath for a simple change of the sample.

Since the sample exchange is easily possible due to the hold from below, the proposed device can also easily be combined with a sample changing system which successively introduces samples into the device, undertakes the optical examination and removes said samples from the device again.

In a further embodiment of the device, the bath has a ring-shaped embodiment, wherein the bath encloses the movable shaft and wherein the movable shaft has a skirt in the form of a beaker opened toward the bottom, which reaches into the bath. Here, the ring-shaped bath surrounds the central region, in which the movable shaft is arranged and can move freely relative to the bath. The skirt of the shaft is connected thereto in a liquid-tight manner or embodied in an integral fashion with the movable shaft. If the cuvette is lowered over the shaft from above, said cuvette surrounds the movable shaft together with the skirt. If a pressure difference is now generated between the interior of the cuvette and the region outside of the cuvette, the fill level of the immersion liquid in the cuvette increases only in the region outside of the skirt. There is no need for a seal between the movable shaft and the bath.

In one embodiment of the device, the means for generating the pressure difference are embodied as bellows, which are filled with a fluid and actuated by a force, as a device for changing the volume of a space filled with a fluid, as a pump, as a height-adjustable liquid reservoir or as a combination of at least two of these means.

In the case of a pressure difference which causes the immersion liquid to be pressed from the bath into the interior of the cuvette through the gap between the lower side of the cuvette and the bath, the pressure within the cuvette is lower than in the region outside of the cuvette. This can be achieved by virtue of the pressure in the interior of the cuvette being reduced, the pressure in the region outside of the cuvette being increased or both the pressure in the interior of the cuvette being reduced and the pressure in the region outside of the cuvette being increased.

If the pressure in the interior of the cuvette is intended to be reduced, the interior of the cuvette must be closed off from the surroundings because otherwise it is not possible to build up a pressure difference. By way of example, the closure can be brought about by a cover on the top, by walls on the sides and by the immersion fluid on the bottom. If the pressure in the interior of the cuvette is now reduced, immersion liquid is pressed from the bath into the cuvette. The fill level falls again when the pressure is increased again. So that the immersion liquid cannot escape by way of the connection between the means for generating the pressure difference and the interior of the cuvette, the opening of the connection into the cuvette should be arranged as high up as possible, but at least as high as the maximum desired fill level.

If the pressure is intended to be increased in the region outside of the cuvette, this region must be delimited from the surroundings by way of a suitable housing. To this end, the housing must completely surround the region of the bath which is not yet covered by the cuvette. In this case, the region outside of the cuvette corresponds to the region surrounded by the housing. Here, the cuvette must be closed off in relation to the region surrounded by the housing, but it can be open to the surroundings. By way of example, such a housing can be configured as a box which surrounds the bath and has an opening on the upper side, through which the movable shaft can be guided to the outside. The cuvette is likewise guided through this opening during lowering, with a seal being arranged between the cuvette and the box. If the pressure is now increased in the region outside of the cuvette or in the region surrounded by the housing, the immersion liquid is pressed into the cuvette and the fill level of the immersion liquid within the cuvette rises. If the pressure is now reduced in turn, the fill level of the immersion liquid in the cuvette also drops again.

In one variant of the device, the means for generating the pressure difference are embodied as bellows, which are filled with a fluid and actuated by a force. The fluid can be a gas such as e.g. air, nitrogen or $CO_2$. A liquid such as water or the immersion liquid can also be used as fluid. Here, the bellows constitute a closed-off volume, in which the actuating force brings about a volume change by pressing together or pulling apart. The bellows can be connected to the interior of the cuvette or the region outside of the cuvette in such a way that a connection to the fluid contained in the bellows is established. By way of example, this connection can be established by way of a pipe or by way of a tube. If a positive force now acts on the bellows, in the case of which the latter are pressed together, the pressure in the interior of the bellows increases, with the pressure increase being transferred by way of the connection to the interior of the cuvette or the region outside of the cuvette. Conversely, the pressure in the interior of the bellows is reduced when a negative force is applied, in the case of which said bellows are pulled apart. If the bellows are connected to the interior of the cuvette, the fill level of the immersion liquid can be increased by virtue of the pressure being reduced in the bellows and hence also in the interior of the cuvette. If the pressure is increased again, the fill level drops again. If the bellows are connected to the region outside of the cuvette, the fill level of the immersion liquid in the interior of the cuvette can be increased by pressing together the bellows. During the pressing together, the pressure in the bellows is increased, and so the pressure in the region outside of the cuvette or in the region surrounded by the housing also increases by way of the connection, and the immersion liquid is pressed into the cuvette. If the pressure is once again reduced, the fill level also drops again.

In a further variant, the means for generating a pressure difference are embodied as a device for changing the volume of a space filled with a fluid. An example of such a device is a syringe, in which the volume in the interior of the syringe can be modified by way of a movable plunger. The fluid contained in the volume can be a gas such as e.g. air, nitrogen or $CO_2$. It is also possible to use a liquid such as water or the immersion liquid as a fluid. If the volume is reduced, the pressure of the fluid contained therein is increased. If the volume is increased, the pressure is lowered. By way of a connection, e.g. a pipe or a tube, the volume filled with a fluid can be connected to the region outside of the cuvette or to the interior of the cuvette such that the pressure increase or reduction is transmitted. If the volume filled with a fluid is connected to the interior of the cuvette, the fill level of the immersion liquid can be increased by virtue of the volume being enlarged and hence the pressure being reduced in the interior of the cuvette. If the volume filled with a fluid is connected to the region outside of the cuvette, the pressure can now be increased by reducing the volume, wherein the pressure in the region outside of the cuvette or in the region surrounded by the housing also increases by way of the connection. The immersion liquid is pressed into the cuvette such that the fill level within the cuvette increases. If the pressure is now reduced in turn, the fill level also drops again.

In a further variant of the device, the means for generating a pressure difference are embodied as a pump. The pump conveys a fluid, wherein an increased pressure prevails at the output of the pump and a reduced pressure in the fluid prevails at the input of the pump. Depending on the embodiment of the pump, input and output can be interchanged by changing the conveying direction. The fluid can be a gas such as e.g. air, nitrogen or $CO_2$. A liquid such as water or the immersion liquid can also be used as fluid. Various sub-variants are conceivable when pumps are used. Thus, it is firstly possible to connect a pump to the interior of the cuvette or the region outside of the cuvette, wherein the pressure is respectively increased or decreased depending on the conveying direction set. Secondly, it is conceivable to connect one connection of the pump to the interior of the cuvette and the other connection of the pump to the region outside of the cuvette. Depending on the conveying direction, the pressure in the interior of the cuvette would be reduced while the pressure in the region outside of the cuvette would be simultaneously increased, or vice versa. Moreover, the use of a plurality of pumps is conceivable, as a result of which the pressures in the interior of the cuvette and in the region outside of the cuvette are adjustable independently of one another.

In another variant of the device, the means for generating a pressure difference are embodied as a height-adjustable liquid reservoir. The liquid reservoir is initially arranged at a lower position and largely or completely filled with the immersion liquid. Two connections are arranged at the liquid reservoir, one at the upper side and one at the lower side of the reservoir. The connections are preferably embodied as tubes. The lower connection is filled with immersion liquid and opens into the bath. The upper connection is filled with a gas, e.g. air, nitrogen or $CO_2$, and opens into the interior of the cuvette, wherein the opening is arranged above or level with the maximum desired fill level. If the cuvette is lowered into the bath, the fill level of the immersion liquid in the interior of the cuvette can be increased by virtue of the liquid reservoir being lifted. If the liquid reservoir is lowered again, the fill level of the immersion liquid in the interior of the cuvette also drops again. When the liquid reservoir is lifted, immersion liquid flows out of it through the lower connection. In the process, negative pressure is created above the liquid level in the reservoir, which is transferred into the interior of the cuvette by way of the upper connection such that the immersion fluid is pressed out of the bath into the interior of the cuvette. When the liquid reservoir is lowered, the immersion liquid flows from the cuvette into the bath, as a result of which the pressure above the fill level in the cuvette is reduced. The pressure reduction is transferred by the upper line to the interior of the liquid reservoir such that immersion liquid is pressed out of the bath and back into the reservoir.

If the region outside of the cuvette is delimited by a housing, a further variant using a height-adjustable liquid reservoir is conceivable, in which both the reservoir and the cuvette are open to the top. Here, the housing surrounds the bath and it is sealed in relation to the cuvette. A tube is arranged on the lower side of the liquid reservoir, which tube is guided through the housing and opens into the bath below the lower edge of the cuvette. For first-time filling, the liquid can be filled both into the open cuvette and into the reservoir. In both cases, the liquid runs into the bath. As soon as the fill level of the liquid in the bath has reached the lower edge of the cuvette, air can no longer escape from the housing. The reservoir and the interior of the cuvette are connected to one another by way of the tube and the bath, wherein the fill levels both in the cuvette and in the liquid reservoir are the same by equalizing of the hydrostatic pressure. The hydrostatic pressure in the liquid reservoir can be changed by adjusting the height, as a result of which it is possible to adjust the fill level in the cuvette.

Moreover, means for restricting the pressure difference are arranged in one embodiment of the device. By restricting the pressure difference to a predeterminable value, it is possible to restrict the maximum fill level of the immersion liquid in the interior of the cuvette. Moreover, it is possible to avoid a further pressure increase or pressure drop after the cuvette was completely filled or emptied. Such a further pressure increase or drop could damage the device or the sample to be examined.

In one embodiment of the device, the means for restricting the pressure difference are embodied in such a way that subsequent liquid which follows the set fill level being reached flows out of the device. This renders it possible to rinse the device by supplying fresh liquid and remove old liquid from the device. A continuous supply of fresh liquid is also conceivable if the liquid is an incubation liquid and/or if the liquid is used for the temperature-control of the sample.

In one embodiment of the device, the means for restricting the pressure difference are embodied as a liquid column, as a pressure control valve, as an overflow or as a combination of at least two of these means.

By way of example, a pressure control valve can be arranged at the connection between the means for generating a pressure difference and the interior of the cuvette or the region outside of the cuvette. If the region outside of the cuvette is surrounded by a housing, the pressure control valve can also be arranged at the housing.

A liquid column for restricting the pressure can for example be realized by way of a container with an overflow, which is filled up to this overflow with liquid and which has a pipe which opens into the liquid in the region of the base of the container. The pipe is connected, for example by way of a tube, to the region, the positive pressure of which is intended to be restricted. Fluid, such as e.g. air, can only escape via the tube and the pipe when the pressure thereof is greater than the hydrostatic pressure of the liquid column which acts between the opening of the pipe and the liquid fill level in the container. The overflow in the container ensures that the height of the liquid column cannot increase if the fluid under pressure is a liquid and flows into the container via the tube and pipe.

By way of example, an overflow can be arranged in the upper region of the cuvette, level with the maximum desired fill level of the liquid in the cuvette. If more liquid is pressed into the interior of the cuvette, it is drained again via the overflow. There cannot be a further increase in pressure.

If a liquid reservoir is used, it is also possible to provide a bypass into the liquid reservoir for restricting the pressure, which bypass enables flowing-over of the liquid above a specific fill level or above a predetermined pressure.

Moreover, it is conceivable to arrange a sensor for monitoring the pressure into the device and bring about relief with the aid of the means for generating a pressure difference if a predetermined limit is exceeded.

In one embodiment of the device, the latter moreover comprises a fill level regulation apparatus, which is configured to regulate the fill level of the liquid in the cuvette.

By way of the fill level regulation device it is possible to compensate for variations in the fill level of the immersion liquid in the interior of the cuvette. These can be created, firstly, by virtue of parts of the liquid being lost due to evaporation; secondly, these can be caused by pressure variations. The pressure variations in turn can be created by e.g. temperature changes in the device. If evaporation can be neglected, the fill level regulation apparatus can be embodied as a pressure regulation apparatus which keeps the pressure difference constant between the interior of the cuvette and the region outside of the cuvette at the value required for the desired fill level. If evaporation is also to be taken into account, it is preferable to arrange a sensor for measuring the fill level of immersion liquid in the interior of the cuvette and to use this measured value as an input variable for a controller. Then, the controller can set the required pressure difference as a manipulated variable with the aid of the means for generating the pressure difference. Any controller known to a person skilled in the art can be used as a controller, in particular a proportional integral differential controller, a proportional integral controller or a pure proportional controller.

Moreover, it is conceivable to use both a controller for the fill level of the immersion liquid in the cuvette and a pressure controller. In this case, it is preferable for a sensor for the pressure at the means for generating the pressure difference and a fill level sensor to be arranged at the cuvette and for the pressure controller to be disposed downstream of the fill level controller. As input variables, the fill level controller receives the setpoint fill level and the actually measured fill level and generates a manipulated variable for the pressure therefrom, which in turn is prescribed to the pressure controller as setpoint pressure. The pressure controller disposed downstream then establishes the required manipulated variable for setting the pressure from the setpoint pressure and the measured pressure.

In a further variant of the device, valves are arranged at the connection between the means for generating a pressure difference and the interior of the cuvette or the region outside of the cuvette. These valves can be closed after reaching the desired pressure difference or after reaching the desired fill level of the immersion liquid in the interior of the cuvette. As a result, a change in the fill level due to pressure variations is reduced.

In a further embodiment, the device comprises an optical access which is substantially aligned horizontally. What this means is that the beam direction of the light used to irradiate the sample or emitted by the sample extends substantially in the horizontal direction. Since the device is usually set up on a table or worktop, the most space available for optical components is along the horizontal plane and the alignment and adjustment of which optical components is easy to bring about in the case of beam paths extending in the horizontal plane. Moreover, it is advantageous in the case of examinations which require a rotation of the sample for this rotation to take place about an axis perpendicular to gravity. This avoids a deformation of the sample. Here, the sample can easily be observed in a manner perpendicular to the axis of rotation.

In one variant of the device, the optical access is realized by way of an objective arranged outside of the cuvette. To this end, the objective is preferably arranged opposite to a straight wall of the cuvette.

In a further embodiment of the invention, the optical access is embodied as an objective which is let into the wall of the cuvette and sealed in relation to the cuvette.

Here, a movable seal is not mandatory since the relative position between sample and objective can be modified by moving the movable shaft. Alternatively, it is possible to displace the whole cuvette together with the objective in the horizontal plane relative to the sample. The seal between the objective and cuvette therefore need not admit movement. By letting the objective into the wall of the cuvette, it can, firstly, be brought significantly closer to the sample, as a result of which the aperture angle or the numerical aperture of the optical axis improves significantly. Secondly, the light need not pass through the wall of the cuvette on its path to the objective.

In one embodiment of the device, the movable shaft is laterally displaceable, vertically displaceable and/or inclinable in relation to the vertical axis.

Depending on the requirements on the device by the employed optical examination method, the movable shaft can be provided with the necessary movement degrees of freedom. By way of example, a translation in the plane can be made possible by displacement stages. A height adjustment can e.g. be achieved by a round holder, which is provided with a male thread and screwed into a base with a female thread. Depending on how far the holder is screwed in, the holder is situated at a different level. An inclination can be realized e.g. by way of a ball-and-socket joint or by way of a spherical mount of the holder. Since the sample can be moved independently of the cuvette by way of the movable shaft, the movement of the sample is completely decoupled from the optical components.

In one embodiment of the device, the movable shaft is embodied as an optical waveguide or as a hollow shaft with an optical waveguide held in the interior. This renders it possible also to illuminate the sample from below or also to collect light emitted downward by the sample.

In a further embodiment of the device, a lens is arranged at the upper side of the movable shaft. In this case, the sample is preferably fastened in the vicinity of the lens or directly thereon.

If the sample is also intended to be illuminated from above or if light emitted upward should also be collected, it is preferable to arrange an optical window into the cover of the cuvette and completely fill the cuvette with the immersion liquid during the examination. In this case, the immersion liquid guides the light ideally from the sample to the window or vice versa.

In one embodiment of the device, at least part of the wall of the cuvette is mirrored. This renders it possible to feed light emitted by the sample in an undirected manner, which would otherwise remain unused, to detection optics.

In a further embodiment of the device, at least part of the cuvette is embodied as an optical waveguide. In this embodiment, it is conversely likewise possible to guide light originating from the sample through the cuvette to the cover and subsequently to detection optics.

In one embodiment of the device, the bath is subdivided into two concentric regions, wherein the inner region is fillable with the immersion liquid and the outer region is fillable with a liquid that is different to the immersion liquid and wherein a cover is fastened to the cuvette, which cover covers the inner concentric region of the bath and which cover has an edge which reaches into the outer concentric region.

In this embodiment, a liquid which acts in a quickly sterilizing or antiseptic manner is preferably used as the other liquid. As a result of this, a region which is separated from the surroundings, firstly by the cuvette and the bath itself and secondly by the sterilizing liquid, is created after the cuvette was lowered onto the shaft with the sample and the edge of the cover was immersed in the other liquid. As a result of this, the use of further seals for separating the interior of the cuvette, together with the immersion liquid, from the surroundings is not required. The proposed device renders it possible to examine living samples such as e.g. embryos of zebrafish, which may not come into contact with germs. The liquid in the interior of the cuvette in this case simultaneously also serves as incubation liquid.

In a further embodiment of the invention, it is conceivable to fasten the sample not directly on the movable shaft, but rather by way of an intermediate piece. Here, the intermediate piece can be configured to be anchored both on the movable shaft and in the interior of the cuvette. In this case, it is possible to fasten the sample on the intermediate piece and insert it into the cuvette together with a liquid. Prior to examining the sample, the cuvette is lowered together with the intermediate piece and the sample by way of the shaft and completely filled a liquid.

Subsequently, the shaft is displaced upward and anchored with the intermediate piece. In the next step, the anchoring between the intermediate piece and the cuvette is released and the shaft is retracted downward again. Now the sample is accessible for an examination and can be positioned by moving the shaft. After completing the examination, the shaft is initially displaced upward again and the intermediate piece is once again anchored on the cuvette. After detaching the connection between the shaft and the intermediate piece, it is now possible to release the liquid from the cuvette, with the liquid remaining above the intermediate piece and continuing to surround the sample. The sample can then be removed together with the cuvette and remains permanently surrounded by the liquid.

A further aspect of the invention is to provide a method for examining samples in a liquid, comprising the following steps:
  a) fixing the sample to the upper side of a movable shaft, wherein the shaft is surrounded by a bath,
  b) lowering a cuvette that is at least open toward the bottom over the shaft in the direction of the base of the bath, wherein a gap remains between the bath base and cuvette,
  c) filling the bath with the liquid,
  d) generating a pressure difference between the interior of the cuvette and the region outside of the cuvette, wherein the fill level of the liquid in the cuvette is set by setting the pressure difference,
  e) carrying out the examination of the sample, wherein the latter can be moved by moving the shaft.

In the first step a) of the method, the sample to be examined is fixed to the upper side of the movable shaft. The shaft is initially oriented vertically and allows simple working with the sample such that the latter can easily be aligned on, and fastened to, the upper side of the shaft. By way of example, fastening can be brought about by adhesive bonding using an optically transparent adhesive; however, other fastening options, such as e.g. clamping or skewering on a needle, which are known to a person skilled in the art are feasible. If the sample is held on a carrier or an intermediate piece, a magnetic fastening or fastening by screws is also conceivable, depending on the embodiment.

In one variant, the movable shaft is rigidly connected to the bath and configured in such a way that it can be removed from the device together with the bath. This makes it easier to align the sample exactly on the movable shaft.

In the second step b) of the method, the cuvette that is at least open toward the bottom is lowered over the shaft in the direction of the base of the bath, wherein a gap remains between the base of the bath and the lower edge of the cuvette.

In the third step c) of the method the bath is filled with the liquid, wherein said liquid also flows into the interior of the cuvette through the gap between the lower edge of the cuvette and the bath base. However, the fill level of the liquid within the cuvette is initially no higher than in the remainder of the bath.

In one embodiment of the method, the liquid is an immersion liquid.

In the fourth step d), a pressure difference is generated between the interior of the cuvette and the region outside of the cuvette, wherein said pressure difference is selected in such a way that the pressure in the interior of the cuvette is lower than in the region outside of the cuvette, and so the liquid is pressed out of the bath into the interior of the cuvette and the fill level of the liquid in the interior of the cuvette increases. The fill level that sets in depends on the set pressure difference.

In the last step e) of the method, the sample is immersed in the liquid and can be examined. Here, a movement of the sample can be realized by moving the shaft on which the sample is fastened.

After completing the examination, the pressure difference can be lifted again such that the immersion liquid flows out of the cuvette again. After lifting the cuvette off the movable shaft, the sample can be removed again.

In one embodiment of the method, the sample is moved during the examination in accordance with step e) of the method by rotating the movable shaft about a vertical axis. The rotation of the sample is required for many optical examination processes in order to be able to examine the sample from different directions.

In one embodiment of the method, for the purposes of setting the pressure difference, the pressure within the cuvette is lowered in relation to the surrounding pressure and/or the pressure in the region outside of the cuvette is increased in relation to the surrounding pressure. In order to modify the pressure in the region outside of the cuvette, this region must be delimited in relation to the surroundings by means of a suitable housing.

Depending on the variant of the method, the pressure difference can be established, for example, by means of bellows, which are filled with a fluid and actuated by a force, by means of a device for changing the volume of a space filled with a fluid, by means of a pump, by means of a height-adjustable liquid reservoir or by means of a combination of at least two of these means.

In one embodiment of the method, the fill level of the immersion liquid in the cuvette is set with the aid of a controller. This renders it possible, firstly, to compensate for liquid losses, e.g. by evaporation, and, secondly, to compensate for variations due to pressure changes. Here, it is possible, for example, to measure the fill height by way of a sensor and for said fill height to serve as an input variable for the controller.

In a further embodiment of the method, the sample is positioned by laterally and/or vertically displacing and/or inclining the movable shaft in relation to a vertical axis during the optical examination in accordance with step e) of the method. The optics used for the optical examinations are not coupled to the movable shaft, and so an independent movement of the sample relative to the optical components used for the optical examination is possible.

In one embodiment of the invention, SLOT (scanning laser optical tomography), SPIM (single plane illumination microscopy), optical projection tomography (OPT), wide-field microscopy, transmission microscopy, confocal fluorescence microscopy, coherent anti-Stokes Raman scattering (CARS), nonlinear microscopy such as e.g. two or three photon microscopy or microscopy using high harmonics generation (HHG), confocal theta microscopy, fluorescence lifetime imaging microscopy (FLIM), stimulated emission detection microscopy (STED), structured illumination microscopy (SIM), optical coherence tomography (OCT), x-ray microscopy, x-ray tomography, an imaging ultrasound method or digital holography is used for the examination in accordance with step e) of the method.

Moreover, a method for examining samples in a liquid is proposed, comprising the following steps:
a) fixing the sample to the upper side of a movable shaft, wherein the shaft is surrounded by a bath,
b) lowering a cuvette that is at least open toward the bottom over the shaft in the direction of the base of the bath, wherein a gap remains between the bath base and cuvette,
c) filling the bath with a first liquid which has a first density,
d) filling the bath with a second liquid with a second density, wherein the second density is less than the first density such that the weight of the second liquid with the second density acts on the first liquid and presses the latter into the cuvette,
e) carrying out the examination of the sample, wherein the latter can be moved by moving the shaft.

In the first step a) of the method, the sample to be examined is fixed to the upper side of the movable shaft. The shaft is initially oriented vertically and allows simple working with the sample such that the latter can easily be aligned on, and fastened to, the upper side of the shaft. By way of example, fastening can be brought about by adhesive bonding using an optically transparent adhesive; however, other fastening options, such as e.g. clamping, which are known to a person skilled in the art are feasible.

In the second step b) of the method, the cuvette that is at least open toward the bottom is lowered over the shaft in the direction of the base of the bath, wherein a gap remains between the base of the bath and the lower edge of the cuvette.

In the third step c) of the method, the bath is filled with a first liquid that has a first density. The first liquid can also flow into the interior of the cuvette through the gap between the lower edge of the cuvette and the bath base. In one embodiment of the method, the first liquid is an immersion liquid.

In the fourth step d), a second liquid with a second density is put into the bath. Since the second liquid has a lower density, a layered system is formed, wherein the second liquid is situated over the first liquid. A pressure is exerted onto the first liquid by way of the second liquid, by means of which pressure said first liquid is pressed into the interior of the cuvette. The fill level of the first liquid in the interior of the cuvette increases. In one variant, the second liquid has sterilizing or antiseptic properties such that the ingress of germs into the immersion liquid is prevented.

In the last step e) of the method, the sample is immersed in the liquid and can be examined. Here, a movement of the sample can be realized by moving the shaft on which the sample is fastened. In one embodiment of the method, an optical method is used to examine the sample.

A further aspect of the invention lies in the use of the proposed device for examining a sample by means of SLOT (scanning laser optical tomography), SPIM (single plane illumination microscopy), optical projection tomography (OPT), wide-field microscopy, transmission microscopy, confocal fluorescence microscopy, coherent anti-Stokes Raman scattering (CARS), nonlinear microscopy such as e.g. two or three photon microscopy or microscopy using high harmonics generation (HHG), confocal theta microscopy, fluorescence lifetime imaging microscopy (FLIM), stimulated emission detection microscopy (STED), structured illumination microscopy (SIM), optical coherence tomography, x-ray microscopy, x-ray tomography, an imaging ultrasound method or digital holography.

ADVANTAGES OF THE INVENTION

In the proposed device, the sample is held from below by way of the movable shaft, and so it is not mounted against gravity. Here, the sample can be completely immersed in a liquid, in particular an immersion liquid and it can be moved by way of the shaft without a movable seal being required between the movable shaft and the sample. At the same time, the arrangement enables simple access to the sample. The space around the sample is completely free and can be used for optical components. Since no seals are necessary, the selection of the optimum immersion liquid by the user is no longer restricted by the compatibility of the immersion liquid with the seal materials.

The complete decoupling of the movement of the sample from the cuvette moreover renders it possible to let parts of the optical components required for the examination, such as e.g. an objective, into the wall of the cuvette and hence maximize the usable numerical aperture. A movable seal for allowing a movement of the objective relative to the cuvette is not required as a result of the decoupling from the movement of the sample. This renders it possible, firstly, to select the immersion liquid without considering the compatibility thereof with the sealing material and, secondly, to carry out the relative positioning between sample and objective more precisely since there is no friction by the seal.

Moreover, as a result of the good accessibility of the sample, the latter can be centered more precisely on the shaft, and so the movement of the sample is not eccentric during a rotation. This improves the quality of the obtained data, the manageability and the sensitivity of the measurement.

In a further embodiment variant, a cover is fastened to the cuvette, which cover is immersed in a second liquid with the edge thereof. This second liquid preferably has antiseptic properties and prevents the ingress of germs into the immersion liquid, once again without a seal being required herefor.

BRIEF DESCRIPTION OF THE DRAWINGS

Exemplary embodiments of the invention are depicted in the drawings and explained in more detail in the following description.

In detail.

EMBODIMENTS

Figure 1:
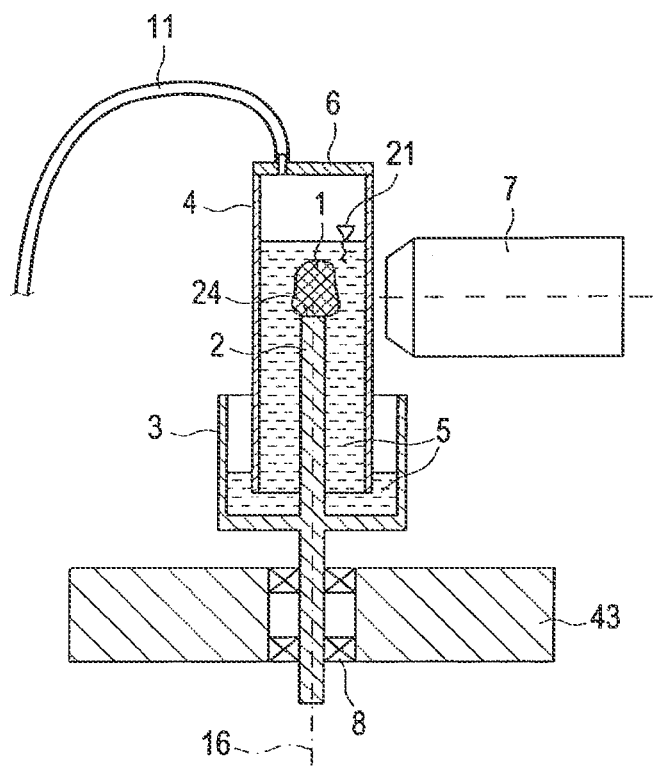
FIG. 1 shows an embodiment of the device with a pressure connection at the cuvette and a separate objective as an optical access.

FIG. 1 shows an embodiment of the device for examining samples in a liquid, with a pressure connection at the cuvette and a separate objective as an optical access.

FIG. 1 shows a sample 1, which is fastened to a sample receptacle 24 of a movable shaft 2. By way of example, the samples can be fastened to the movable shaft 2 by adhesive bonding using an optically transparent adhesive. Further fastening options, such as e.g. clamping, are likewise conceivable. The shaft 2 is surrounded by a bath 3 which, in the embodiment depicted in FIG. 1, is embodied as an upwardly open beaker and rigidly connected to the shaft 2. The shaft 2 and the bath 3 are held in a rotatable manner in a holder 43 by way of the bearing 8.

Before carrying out an optical examination of the sample 1, a cuvette 4 is placed over the shaft 2 such that a gap remains between the lower side of the cuvette 4 and the base of the bath 3. The cuvette 3 has a cover 6, at which a tube 11 opens into the interior of the cuvette 4. The tube 11 is connected to a means for generating a pressure difference. By way of example, bellows, which are filled with a fluid and actuated by a force, a device for changing the volume of a space filled with a fluid, a pump, a height-adjustable liquid reservoir or a combination of at least two of these means is/are suitable as means for generating the pressure difference.

In the situation depicted in FIG. 1, the bath 3 was filled with an immersion liquid 5 and the pressure within the cuvette 4 was subsequently lowered in relation to the pressure outside of the cuvette 4 such that the immersion liquid 5 is pressed out of the bath 3 and into the interior of the cuvette 4, and completely surrounds the sample 1. By way of a suitable selection of the pressure difference, it is possible to set the fill level 21 of the immersion liquid 5 in the interior of the cuvette 4.

For the purposes of carrying out the optical examination, an objective 7 is arranged outside of the cuvette 4, aligned horizontally with the sample 1, in the embodiment depicted in FIG. 1. Since the objective 7 is not coupled to the sample 1, it can be moved freely in relation to the latter. Depending on the examination process employed, it is also possible to arrange further optical components around the cuvette 4. The sample 1 can be rotated about the vertical axis 16, which in this case coincides with the axis of the shaft 2, during the examination by rotating the shaft 2 in the bearing 8. After the optical examination is complete, the pressure in the interior of the cuvette 4 can be normalized by way of the tube 11 such that the immersion liquid 5 flows back into the bath 3. Subsequently, it is possible to lift the cuvette 4 and change the sample 1.

The dimensions of the bath 3 are preferably selected in such a way that the latter can hold all of the immersion liquid 5 from the cuvette 4. Alternatively, the bath 3 is provided with a drain and the drained immersion liquid 5 is replaced in the next pass.

In a further embodiment, it is conceivable to arrange a valve between the tube 11 and the means for generating a pressure difference, which valve is closed when the desired fill level 21 of the immersion liquid 5 is reached in the interior of the cuvette 4. This renders it possible to prevent pressure variations from being transmitted to the fill level 21 of the immersion liquid 5.

Figure 2:
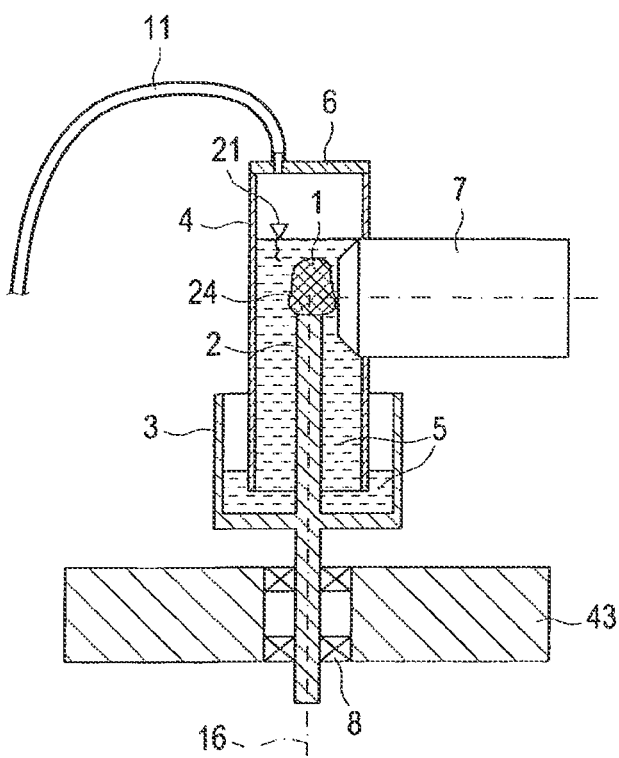
FIG. 2 shows a further embodiment of the device with a pressure connection at the cuvette and an objective let into the wall of the cuvette.

FIG. 2 shows an embodiment of the device for examining samples in a liquid, with a pressure connection at the cuvette and an objective let into the wall of the cuvette.

FIG. 2 shows a sample 1 which is fastened to the upper side 24 of a movable shaft 2. By way of example, the sample 1 can be fastened to the movable shaft 2 by adhesive bonding using an optically transparent adhesive. Further fastening options, such as e.g. clamping, are likewise conceivable. The shaft 2 is surrounded by a bath 3 which, in the embodiment depicted in FIG. 2, is embodied as an upwardly open beaker and rigidly connected to the shaft 2. The shaft 2 and the bath 3 are held in a rotatable manner in a holder 43 by way of the bearing 8.

As described in FIG. 1, a cuvette 4 is placed over the shaft 2 and said cuvette is connected to a means for generating a pressure difference by way of the tube 11. Immersion liquid 5 was pressed from the bath 3 into the interior of the cuvette 4 and the fill level 21 was set by generating a negative pressure. In order to carry out the optical examination, an objective 7 is let into the wall of the cuvette 4 and aligned horizontally onto the sample 1 in the embodiment depicted in FIG. 2. The objective 7 is sealed in relation to the wall of the cuvette 4, for example using an elastomeric seal or the objective 7 is adhesively bonded into the wall. Moreover, it is conceivable not to integrate the objective 7 into the wall of the cuvette 4 by way of an opening, but to optically couple the objective, for example via an air gap, by means of immersion liquid, by bursting or by cementing onto the cuvette. Moreover, it is conceivable to receive the objective 7 in a holder and screw it to the cuvette 4.

The sample 1 can be rotated about the vertical axis 16, which in this case coincides with the axis of the shaft 2, during the examination by rotating the shaft 2 in the bearing 8. Since the objective 7 is decoupled from the sample 1, it is moreover conceivable to displace the whole cuvette 4, together with the objective 7, relative to the sample 1 in the horizontal plane. Depending on the employed examination process, it is also possible to arrange further optical components around the cuvette 4.

Figure 3:
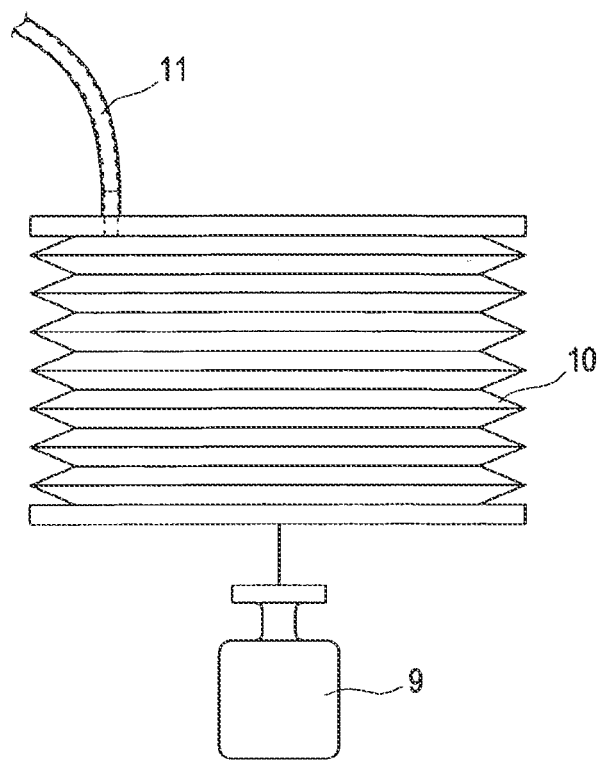
FIG. 3a shows bellows with a weight hanging therefrom.
FIG. 3b shows bellows with a weight placed thereon.
Figure 3:
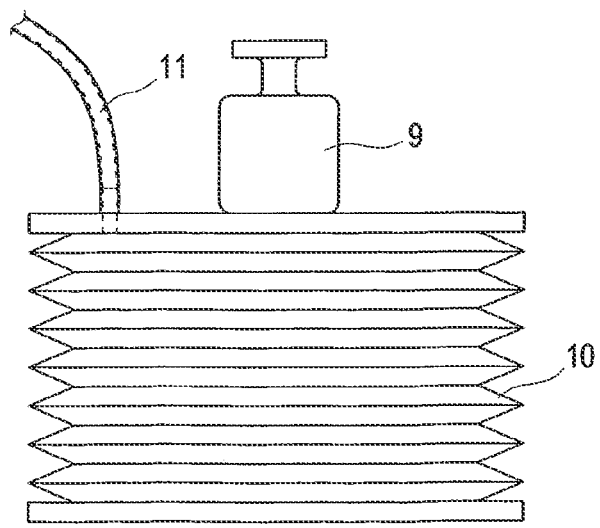

FIGS. 3a and 3b each show bellows, once with a weight hanging therefrom (3a) and once with a weight placed thereon (3b).

FIGS. 3a and 3b show a possible functional principle for the means for generating a pressure difference. Bellows 10, which are constructed from a tube made of an elastic material folded in the style of an accordion, are closed-off at the top and bottom. The bellows 10 surround a volume which is filled with a fluid, for example air, nitrogen or $CO_2$. At the upper end, the bellows 10 are connected to a tube 11. The tube opens into a region in which the pressure is intended to be increased or lowered.

FIG. 3a depicts how the pressure can be reduced using the bellows 10. To this end, a downward-directed force is applied to the lower end of the bellows 10, depicted in FIG. 3a by attaching a weight 9, while the upper end is fixed. The acting force causes the bellows 10 to be pulled apart, leading to an increase of the volume contained in the bellows 10 and hence to a reduction in pressure in the held fluid. By way of example, if the bellows 10 are connected to the interior of the cuvette, the pressure within the cuvette is also reduced. Immersion fluid flows into the interior of the cuvette.

FIG. 3b depicts how the pressure can be increased using the bellows 10. To this end, a downward-directed force is applied to the upper end of the bellows 10, depicted in FIG. 3b by placing a weight 9 thereon, while the lower end is fixed. The acting force causes the bellows 10 to be pressed together, leading to a reduction of the volume contained in the bellows 10 and hence to an increase in pressure in the held fluid. By way of example, if the bellows 10 are connected to the interior of the cuvette, the pressure within the cuvette is also increased. The immersion liquid is displaced from the interior of the cuvette.

Figure 4:
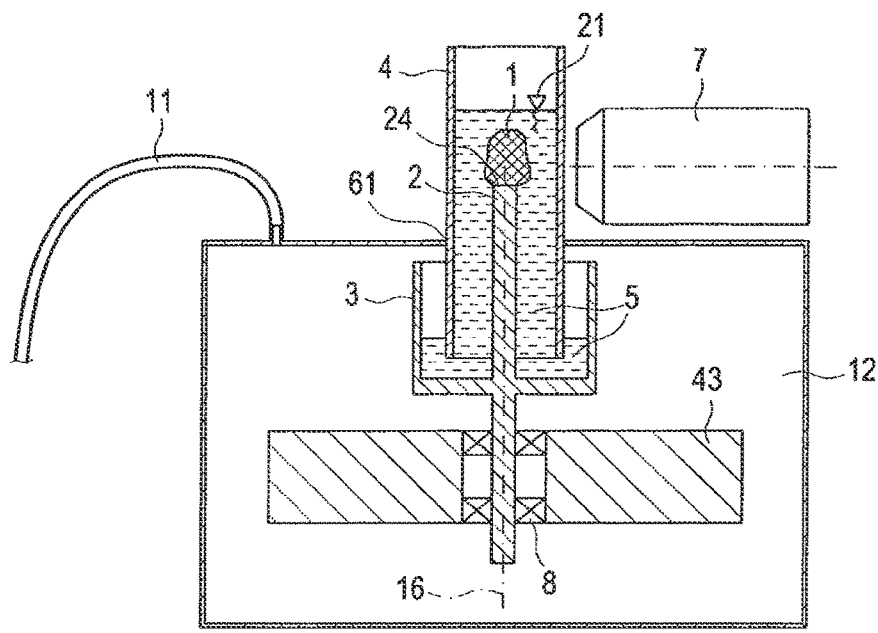
FIG. 4 shows an embodiment of the device with a housing.

FIG. 4 shows an embodiment of the device for examining samples in a liquid, with a housing.

FIG. 4 depicts a sample 1, which is fastened to the upper side 24 of a movable shaft 2. By way of example, the sample 1 can be fastened to the movable shaft 2 by adhesive bonding using an optically transparent adhesive. Further fastening options, such as e.g. clamping, are likewise conceivable. The shaft 2 is surrounded by a bath 3 which, in the embodiment depicted in FIG. 4, is embodied as an upwardly open beaker and rigidly connected to the shaft 2. The shaft 2 and the bath 3 are held in a rotatable manner in a holder 43 by way of the bearing 8. Together with the bearing 8 and the holder 43, the bath 3 is held in a housing 12, which has an opening 61 at the upper side thereof, through which the shaft 2 protrudes to the outside from the interior of the housing 12.

Before carrying out the optical examination, a cuvette 4 is placed from above over the movable shaft 2 through the opening 61 in the housing 12 and it is lowered to just above the base of the bath 3. Here, a gap remains between the lower edge of the cuvette 4 and the base of the bath 3. In the depicted embodiment, the cuvette 4 is open both toward the bottom and toward the top. In the opening 61, the cuvette 4 is sealed against the housing 12. Moreover, a tube 11, by means of which a means for generating a pressure difference can be connected to the housing 12, is arranged in the upper region of the housing 12.

The bath 3 is still empty prior to the first filling of the cuvette 4 with immersion liquid 5. The immersion liquid 5 is filled into the device by way of the cuvette 4 that is open toward the top. Here, the immersion liquid 5 is initially distributed uniformly over the whole bath 3 through the gap between the cuvette 4 and the base of the bath 3 as air that is contained in the housing 12 can likewise still escape to the outside through the open cuvette 4 by way of this gap. As soon as the fill level 21 of the immersion liquid 5 exceeds the height of the gap, air can no longer escape from the housing 12. The air pressure in the interior of the housing 12 increases and prevents more of the immersion liquid 5 from flowing into the bath 3, and so the immersion liquid 5 now remains in the interior of the cuvette 4. The filling process can be completed as soon as the sample 1 is completely immersed in the immersion liquid 5.

In order to lower the fill level of the immersion liquid 5 in the cuvette 4, the pressure within the housing 12 is lowered by way of the means for generating a pressure difference that are connected to the housing 12 via the tube 11. The immersion fluid 5 now flows from the cuvette 4 into the bath 3 by way of the gap between the lower edge of the cuvette 4 and the base of the bath 3.

The fill level 21 of the immersion liquid 5 in the interior of the cuvette 4 can be raised again by virtue of the pressure within the housing 12 being raised again by way of the means for generating a pressure difference via the tube 11. The fill level 21 can be set by selecting the pressure.

For the purposes of carrying out the optical examination, an objective 7 is arranged outside of the cuvette 4, aligned horizontally with the sample 1, in the embodiment depicted in FIG. 4. Since the objective 7 is not coupled to the sample 1, it can be moved freely in relation to the latter. Depending on the examination process employed, it is also possible to arrange further optical components around the cuvette 4. The sample 1 can be rotated about the vertical axis 16, which in this case coincides with the axis of the shaft 2, during the examination by rotating the shaft 2 in the bearing 8.

Since the cuvette 4 is open toward the top in this embodiment, access to the sample 1 is possible, even during the examination. If part of the housing 12 moreover has a flexible embodiment, e.g. as bellows, a movement of the cuvette 4 is moreover also possible. Here, it is conceivable in a further variant of the device that the objective 7 is let into the wall of the cuvette 4 like in the embodiment in FIG. 2 or that the objective 7 is coupled by way of a holder to the cuvette 4 and the objective 7 is moved together with the cuvette 4.

Figure 5:
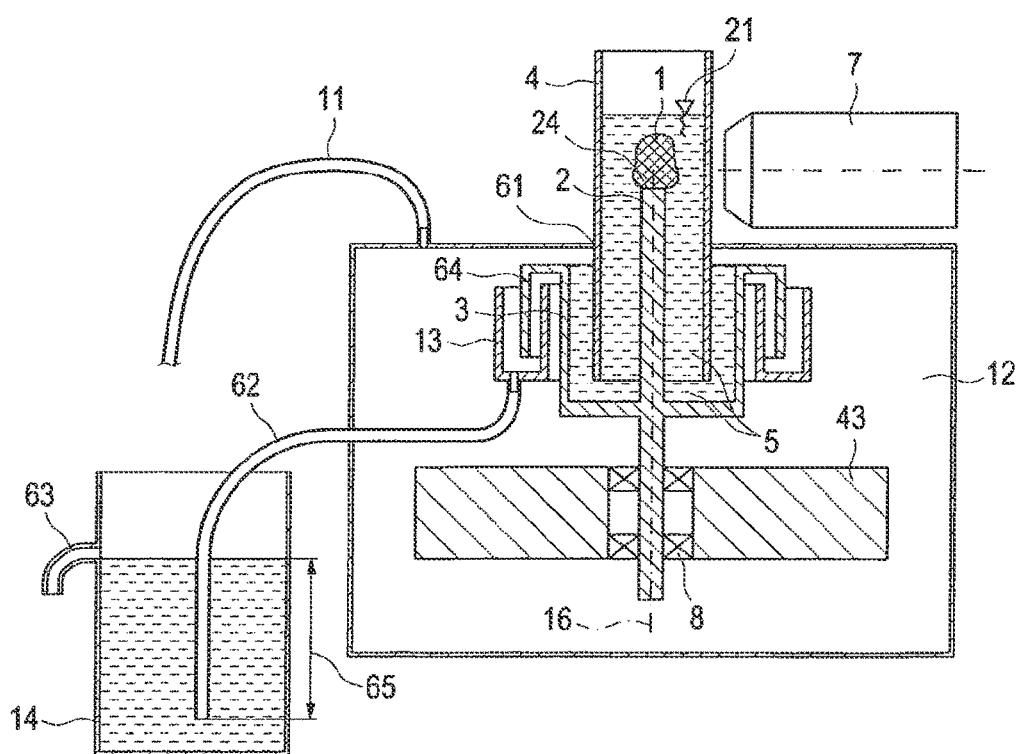
FIG. 5 shows a further embodiment of the device with a housing and a liquid column for restricting the pressure.

FIG. 5 shows a further embodiment of the device for examining samples in a liquid, with a housing and a liquid column for restricting the pressure.

FIG. 5 depicts a sample 1, which is fastened to the upper side 24 of a movable shaft 2. By way of example, the sample 1 can be fastened to the movable shaft 2 by adhesive bonding using an optically transparent adhesive. Further fastening options, such as e.g. clamping, are likewise conceivable. The shaft 2 is surrounded by a bath 3 which, in the embodiment depicted in FIG. 5, is embodied as an upwardly open beaker and rigidly connected to the shaft 2. The shaft 2 and the bath 3 are held in a rotatable manner in a holder 43 by way of the bearing 8. A skirt 64 reaching in a ring-shaped overflow bath 13 is held at the outer edge of the bath 3. The overflow bath 13 surrounds the bath 3. Alternatively, the overflow bath 13 can be embodied as a beaker and be arranged below the bath 3.

Together with the bearing 8 and the holder 43, the bath 3 is held in a housing 12, which has an opening 61 at the upper side thereof, through which the shaft 2 protrudes to the outside from the interior of the housing 12. The housing 12 moreover comprises a tube 11, by means of which a connection to a means for generating a pressure difference is established. Moreover, a tube 62 is guided through the wall of the housing 12, which tube opens into the base of the overflow bath 13 at one end and opens into the base region of a vessel 14 at the other end. The vessel 14 comprises an overflow outlet 63 in the upper region.

In a further embodiment, it would also be conceivable for the movable shaft 2 to be guided out of the housing 12 below the bath 3. Here, the seal between the shaft 2 and the housing 12 must be configured to enable a movement of the shaft 2. The bearing 8 and the holder 43 can be arranged outside of the housing 12 in this case.

Before carrying out the optical examination, a cuvette 4 is placed from above over the movable shaft 2 through the opening 61 in the housing 12 and it is lowered to just above the base of the bath 3. Here, a gap remains between the lower edge of the cuvette 4 and the base of the bath 3. In the depicted embodiment, the cuvette 4 is open both toward the bottom and toward the top. In the opening 61, the cuvette 4 is sealed against the housing 12. The bath 3 and the vessel 14 are still empty prior to the first filling of the cuvette 4 with immersion liquid 5. The immersion liquid 5 is filled into the device by way of the cuvette 4 that is open toward the top. Here, the immersion liquid 5 is initially distributed uniformly over the whole bath 3 through the gap between the cuvette 4 and the base of the bath 3. The air that is contained in the housing 12 can escape to the outside through the tube 62. As soon as the fill level 21 of the immersion liquid 5 exceeds the height of the outer edge of the bath 3, immersion liquid 5 flows into the overflow bath 13. From there, the immersion liquid 5 flows into the vessel 14 via the tube 62. Positive pressure starts to build up in the housing 12 as soon as the fill level lies over the opening of the tube 62 in the vessel 14. The positive pressure in the housing 12 allows the fill level 21 of the immersion liquid 5 to increase further in the interior of the cuvette 4, wherein the fill level 21 corresponds precisely to the height of the liquid column 65 between the liquid level in the vessel 14 and the opening of the tube 62 into the vessel 14. If the liquid level in the vessel 14 increases beyond the height of the outflow outlet 63, it can no longer rise further since the additional immersion liquid is drained from the vessel 14 via the overflow outlet 63. The filling process can now be completed since the liquid column 65 restricts the positive pressure in the interior of the housing 12, and hence the maximum fill level 21 in the cuvette 4.

Alternatively, the vessel 14 can already be filled prior to the first filling of the cuvette 4. As a result, an overflow of the liquid 5 into the overflow bath 13 from the bath 3 is prevented for as long as the maximum fill level in the cuvette 4, predetermined by the liquid column 65, is not exceeded.

In a further variant of the device, it is conceivable not to provide a separate overflow bath 13. In this variant, the immersion liquid 5 flows out of the bath 3 to the base of the housing 12 and, from there, into the vessel 14 via the tube 62.

In order to lower the fill level of immersion liquid 5 in the cuvette 4, the pressure within the housing 12 is lowered by way of the means for generating a pressure difference connected to the housing 12 via the tube 11. The immersion fluid 5 now flows out of the cuvette 4 into the bath 3 via the gap between the lower edge of the cuvette 4 and the base of the bath 3, with excessive liquid being drained by way of the overflow bath 13.

The fill level 21 of the immersion liquid 5 in the interior of the cuvette 4 can be lifted again by virtue of the pressure within the housing 12 being lifted again by the tube 11 by way of the means for generating a pressure difference. Immersion liquid is then pressed back into the interior of the cuvette 4 from the bath 3. The fill level 21 can be set by selecting the pressure.

Moreover, it is possible to rinse the device by virtue of a large amount of fresh liquid 5 being filled into the cuvette 4. The fresh liquid 5 displaces the old liquid from the cuvette 4 into the bath 3. The liquid 5 is drained from the bath 3 into the overflow bath 13 and finally drained in the vessel 14 via the tube 62 and the overflow outlet 63. Rinsing is preferably carried out continuously by virtue of fresh liquid 5 being filled into the device continuously. As a result, the sample 1 can be supplied continuously with the nutrient solution; furthermore, it is thus possible to keep the sample 1 at a specific temperature or else to modify the temperature when supplying a temperature-controlled medium.

In order to carry out the optical examination, it is possible to proceed as described in relation to FIG. 4.

Figure 6:
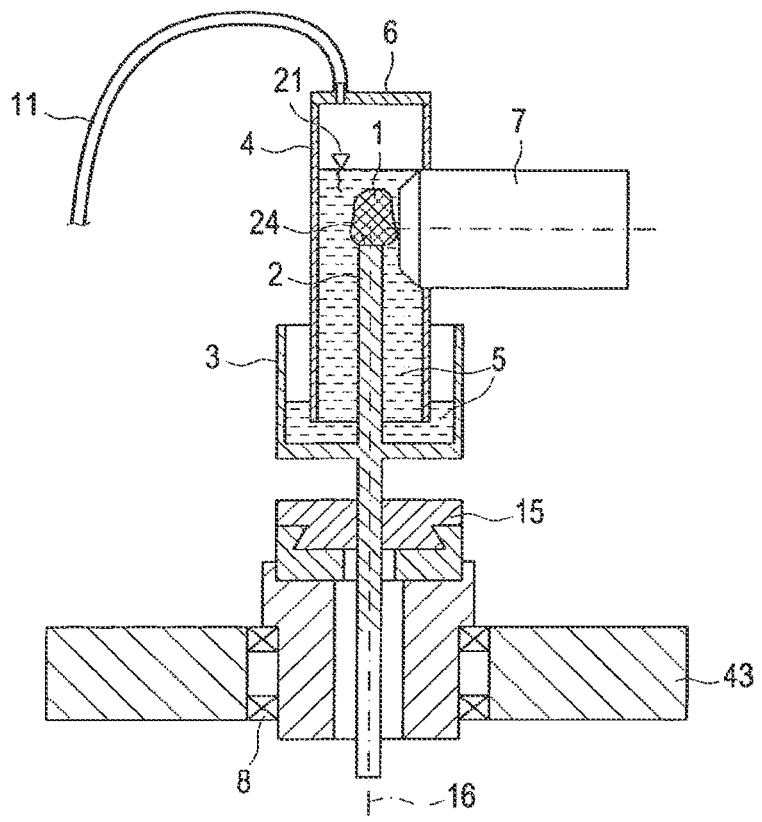
FIG. 6 shows an embodiment of the device with a laterally movable shaft.

FIG. 6 shows an embodiment of the device for examining samples in a liquid, with a laterally movable shaft.

FIG. 6 shows a sample 1 which is fastened to the upper side 24 of a movable shaft 2. By way of example, the sample can be fastened to the movable shaft 2 by adhesive bonding using an optically transparent adhesive. Further fastening options, such as e.g. clamping, are likewise conceivable. The shaft 2 is surrounded by a bath 3 which, in the embodiment depicted in FIG. 6, is embodied as an upwardly open beaker and rigidly connected to the shaft 2. The shaft 2 and the bath 3 are mounted on a displacement stage 15, which permits a translation or displacement of the movable shaft 2. The displacement stage 15 in turn is held in a rotatable manner in a holder 43 by way of the bearing 8.

Before an optical examination is carried out on the sample 1, a cuvette 4 is placed over the shaft 2 such that a gap remains between the lower side of the cuvette 4 and the base of the bath 3. The cuvette 3 has a cover 6, at which a tube 11 opens into the interior of the cuvette 4. The tube 11 is connected to a means for generating a pressure difference. By way of example, bellows, which are filled with a fluid and actuated by a force, a device for changing the volume of a space filled with a fluid, a pump, a height-adjustable liquid reservoir or a combination of at least two of these means is/are suitable as a means for generating a pressure difference.

As already described in relation to FIG. 2, a cuvette 4 is placed over the shaft 2 and said cuvette is connected to a means for generating a pressure difference via the tube 11. In order to carry out the optical examination, an objective 7 is let into the wall of the cuvette 4 and aligned horizontally onto the sample 1 in the embodiment depicted in FIG. 6.

By rotating the shaft 2, the sample 1 can be rotated together with the displacement stage 15 about a vertical axis 16 by way of the bearing 8 during the examination. Additionally, it is possible to displace the movable shaft 2 in a lateral direction by way of the displacement stage 15. In further embodiments, it is conceivable to arrange a second displacement stage in a manner rotated by 90° in order to be able to displace the movable shaft 2 along both lateral directions. It is likewise conceivable to arrange the bearing 8 on the displacement table 25 such that the movable shaft 2 can be displaced together with the axis of rotation.

In a further embodiment, it is possible to displace the whole cuvette 4, together with the objective 7, in the horizontal plane relative to the sample 1. Depending on the examination process used, it is also possible to arrange further optical components around the cuvette 4.

Figure 7:
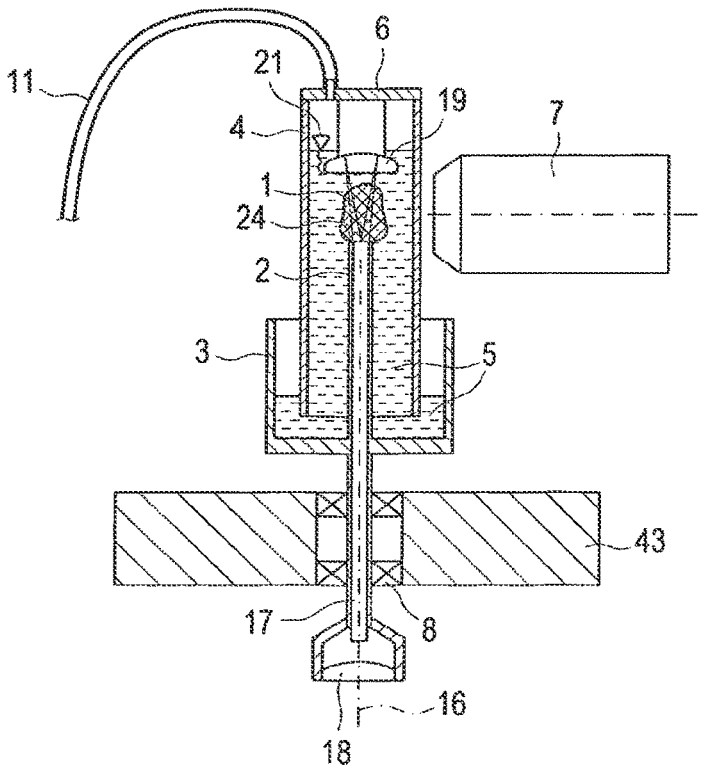
FIG. 7 shows an embodiment of the device with an optical waveguide included in the movable shaft.

FIG. 7 shows an embodiment of the device for examining samples in a liquid, with an optical waveguide included in the movable shaft.

The device shown in FIG. 7 substantially corresponds to the arrangement already described in relation to FIG. 1; however, the embodiment depicted in FIG. 7 has additional optical components. In addition to the objective 7 arranged outside of the cuvette 4, an elliptic reflector 19 is arranged within the cuvette 4. The movable shaft 2 is embodied as a hollow shaft and it includes an optical waveguide 17 in the interior thereof. The optical waveguide 17 is sealed in relation to the shaft 2 and can be embodied, for example, in the form of a glass rod, a liquid optical waveguide, a bundle of fibers or an internally reflecting hollow body. As depicted in FIG. 7, the sample 1 can be arranged directly on the optical waveguide 17. Moreover, it is conceivable to insert collecting optics or an objective between the sample 1 and the optical waveguide 17. If an objective is used, it is sufficient to embody the shaft 2 as a hollow shaft since in this case it can directly pass the light, without being reflective on the inside.

Condenser optics 18 are preferably arranged at the lower end of the shaft 2 in order to collect the light emerging from the shaft 2 and feed the latter to detection optics.

In the example depicted in FIG. 7, light can be radiated into the sample 1 from below by way of the shaft 2. Light emitted upward from the sample is reflected at the elliptic reflector 19 and coupled into the optical waveguide 17.

In further embodiments, it is possible to use a spherical reflector or a parabolic reflector instead of the elliptic reflector 19.

Figure 8:
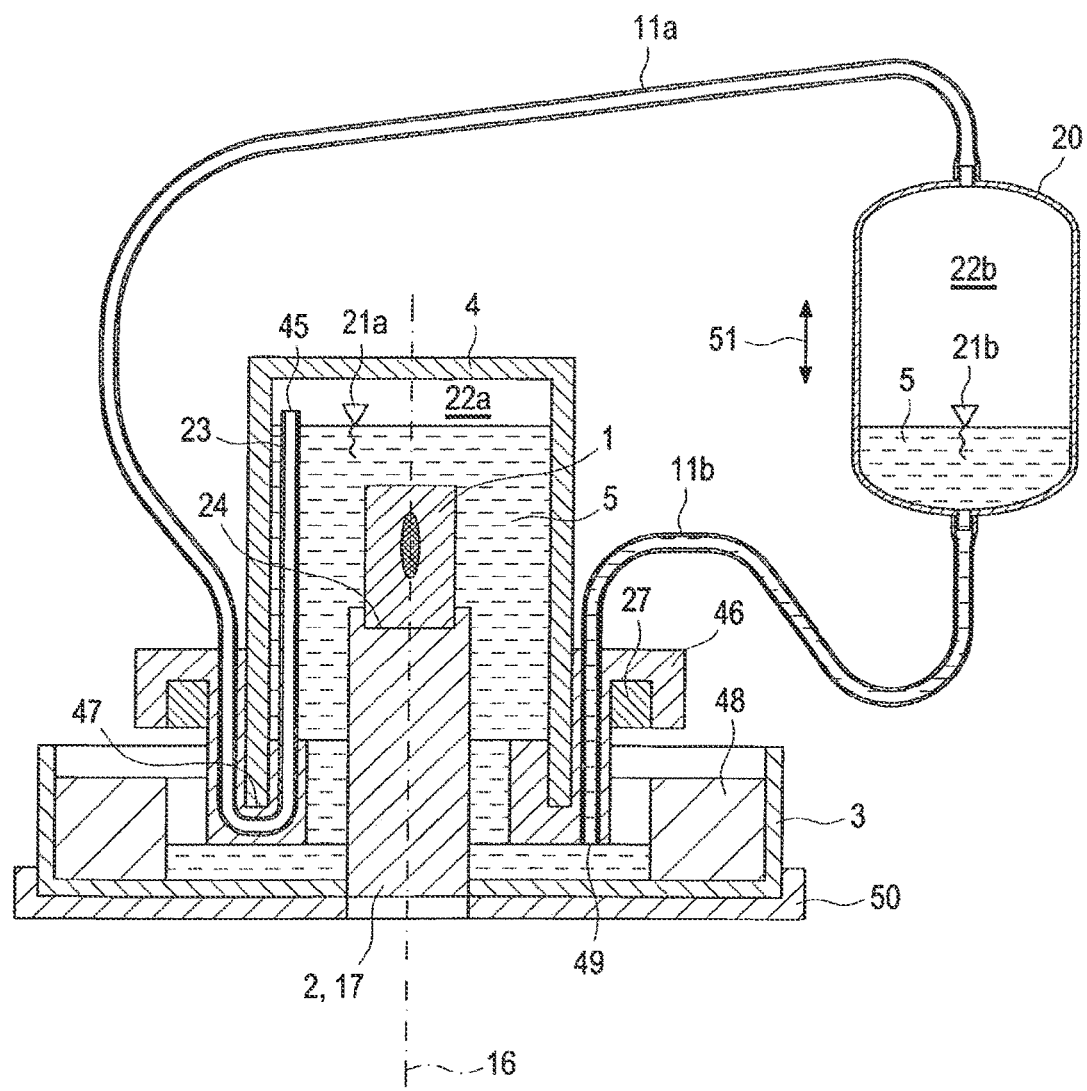
FIG. 8 shows an embodiment of the device with a liquid reservoir.

FIG. 8 shows an embodiment of the device for examining samples in a liquid, with a liquid reservoir.

FIG. 8 depicts a sample 1 which was fastened to the movable shaft 2 for the examination. In order to simplify the arrangement of the sample, a depression into which the sample 1 can be inserted is provided at the upper side 24 of the movable shaft 2. By way of example, a transparent adhesive can be used to fix the sample 1. The movable shaft 2 is let into the base of the bath 3 at the lower end thereof and rigidly connected to the latter. In the embodiment depicted in FIG. 8, the movable shaft 2 is embodied as an optical waveguide 17 and it also enables an optical access to the sample 1 from below. The bath 3 is placed onto a rotary table 50, which enables a rotation about the vertical axis 16, which in this case coincides with the axis of the shaft 2. The connection between the rotary table 50 and the bath 3 is embodied as an interlocking fit or any other detachable connection such that the bath 3 can be removed together with the movable shaft 2.

In the embodiment depicted in FIG. 8, the device moreover comprises an adapter 46, which has a groove 47 in which a cuvette 4 is held. By way of example, the cuvette 4 is sealed in relation to the adapter 46 by way of an elastomeric seal or by adhesive bonding. Two tubes 11a and 11b, which are connected to a height-adjustable liquid reservoir 20, open into the adapter 46. The first tube 11a opens into the liquid reservoir 20 at the upper side while the second tube 11b opens into the liquid reservoir 20 at the lower side. The first tube 11a merges into an air pipe 23 at the adapter 46, which air pipe has an opening 46 in the upper region of the cuvette 4. The second tube 11b has an opening 47 at the lower end of the adapter 46.

The adapter 46 is mounted on a height-adjustable fork such that said adapter can be lowered over the movable shaft 2 together with the cuvette 4. After lowering, a gap through which liquid can flow remains between the lower side of the adapter 46 and the base of the bath 3. Optical access to the sample 1 is possible from all spatial directions since the walls and the cover of the cuvette 4 are transparent and the movable shaft 2 is embodied as an optical waveguide 17.

Prior to the optical examination of the sample 1, the height-adjustable liquid reservoir 20 is in a lowered position and largely or completely filled with an immersion liquid 5. By lifting the liquid reservoir 20, the immersion liquid 5 is drained downward from the liquid reservoir 20 through the second tube 11b and it reaches the bath 3 through the opening 49 at the lower side of the adapter 46. An air space 22b is created above the fill level 21b in the liquid reservoir 20 as a result of the draining immersion liquid 5. The volume of the air space 22b increases, and so the pressure of the gas contained therein decreases. Therefore, air flows from the interior of the cuvette 4 into the air space 22b of the liquid reservoir 20 by way of the first tube 11a and the air pipe 23. As long as the fill level of the immersion fluid 5 in the bath 3 has not reached the lower edge of the adapter 46, air can flow into the interior of the cuvette 4 through the gap between the adapter 46 and the base of the bath and compensate the pressure difference being produced. This is no longer possible after the fill level of immersion liquid 5 in the bath 3 has risen so far that the latter closes off the gap. Instead of air, it is now the immersion liquid 5 that is pressed into the interior of the cuvette 4 in order to compensate for the pressure difference. The immersion fluid 5 flows into the interior of the cuvette 4 until the pressure is equalized. This is the case when the fill level 21a of the immersion liquid 5 in the interior of the cuvette 4 equals the fill level 21b of the immersion liquid 5 in the liquid reservoir 20.

The liquid reservoir 20 is lowered again in order to lower the fill level 21a of the immersion liquid 5 in the interior of the cuvette 4. The hydrostatic pressure in the immersion liquid 5 in the interior of the cuvette 4 is now greater than that of the liquid in the reservoir 20, and so the immersion liquid 5 flows from the cuvette 4 into the bath 3. Now the volume of the air space 22a above the fill level 21a in the cuvette 4 increases such that the pressure of the contained gas decreases. Due to the connection via the first tube 11a, the pressure in the air space 22b in the liquid reservoir 20 also decreases. Immersion liquid 5 is now pressed out of the bath 3 and back into the liquid reservoir 20 by way of the second tube 11b in order to equalize the pressure there.

In order to reduce the amount of immersion fluid required in the bath 3, a ring 48 has been inserted into the bath 3 in the embodiment depicted in FIG. 8. A correspondingly smaller bath can also be used in further embodiments.

Moreover, it is conceivable to respectively insert valves at the connection tubes 11a and 11b and close these after the desired fill level 21a was reached such that pressure variations in the liquid reservoir 20, for example due to change in temperature, cannot have an effect on the fill level 21a.

Figure 9:
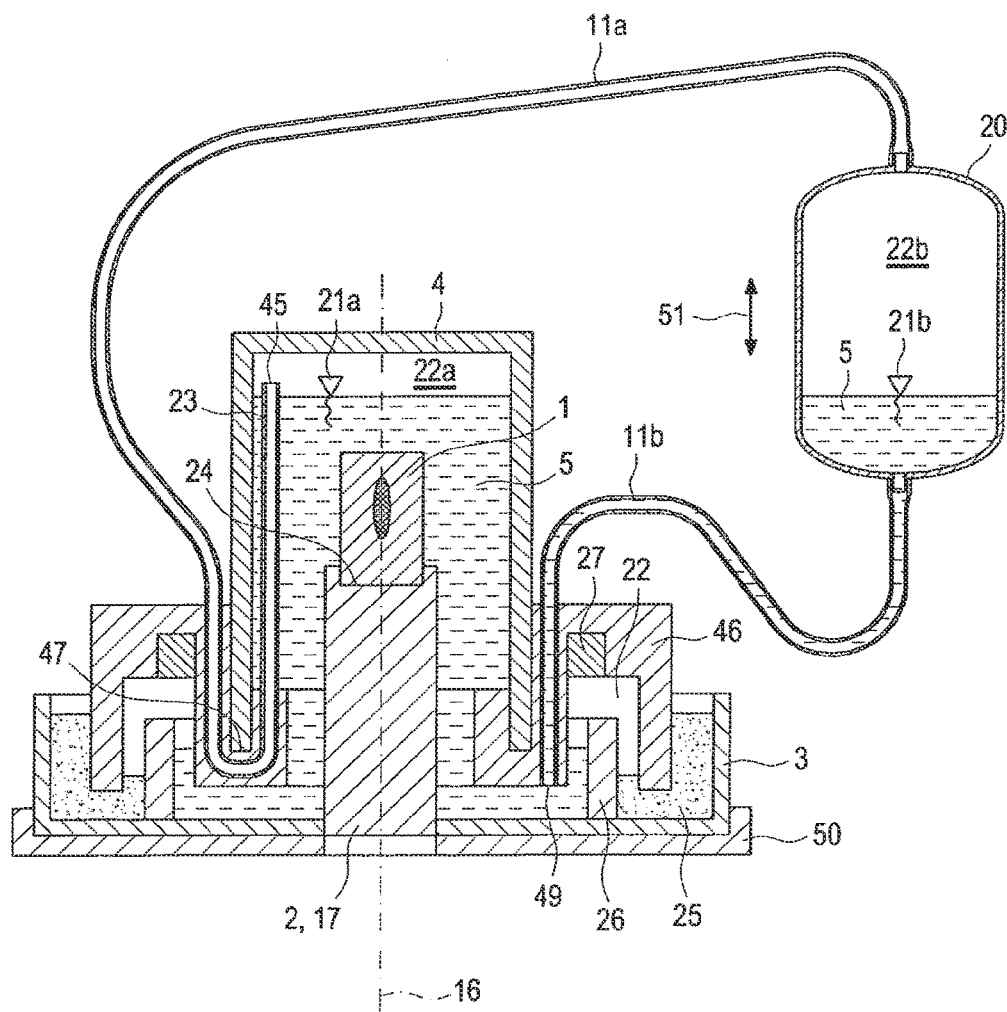
FIG. 9 shows a further embodiment of the device with a liquid reservoir and a subdivided bath.

FIG. 9 shows a further embodiment of the device for examining samples in a liquid, with a liquid reservoir and a bath subdivided into two concentric regions.

FIG. 9 depicts a sample which was fastened to the movable shaft 2 for the examination. In order to simplify the arrangement of the sample, a depression into which the sample can be inserted is provided at the upper side 24 of the movable shaft 2. By way of example, a transparent adhesive can be used to fix the sample 1. The movable shaft 2 is let into the base of the bath 3 at the lower end thereof and rigidly connected to the latter. In the embodiment depicted in FIG. 8, the movable shaft 2 is embodied as an optical waveguide 17 and it also enables an optical access to the sample 1 from below. The bath 3 is placed onto a rotary table 50, which enables a rotation about the vertical axis 16, which in this case coincides with the axis of the shaft 2. The connection between the rotary table 50 and the bath 3 is embodied as an interlocking fit or any other detachable connection such that the bath 3 can be removed easily together with the movable shaft 2. The bath 3 is subdivided into two concentric regions by way of a ring 26, which is sealed against the base of the bath 3.

In order to generate a pressure difference, by means of which the immersion liquid 5 can be pressed into the interior of the cuvette 4, a height-adjustable liquid reservoir 20 is provided, like in the embodiment of FIG. 8. The fill level 21a of the immersion liquid 5 in the interior of the cuvette 4 is likewise set as described in relation to FIG. 8, but the immersion liquid 5 only reaches the inner concentric region of the bath 3.

The outer concentric region of the bath 3 is filled with a second liquid 25, which preferably has antiseptic properties. In order to shield the interior of the cuvette 4 from the surroundings, the adapter 46 has a ring-shaped skirt 66 which, in the lowered state of the adapter 46, reaches in the outer concentric region of the bath 3 and becomes immersed in the antiseptic liquid 25 situated therein. The immersion liquid 5 is now completely sealed-off from the surroundings.

Sealing the immersion liquid 5 from the surroundings is advantageous, particularly if living samples, such as e.g. embryos of zebrafish, are intended to be examined with the aid of the device. The immersion liquid 5 in this case simultaneously serves as an incubation liquid for the sample 1 and it must not be contaminated by germs from the surroundings.

Figure 10:
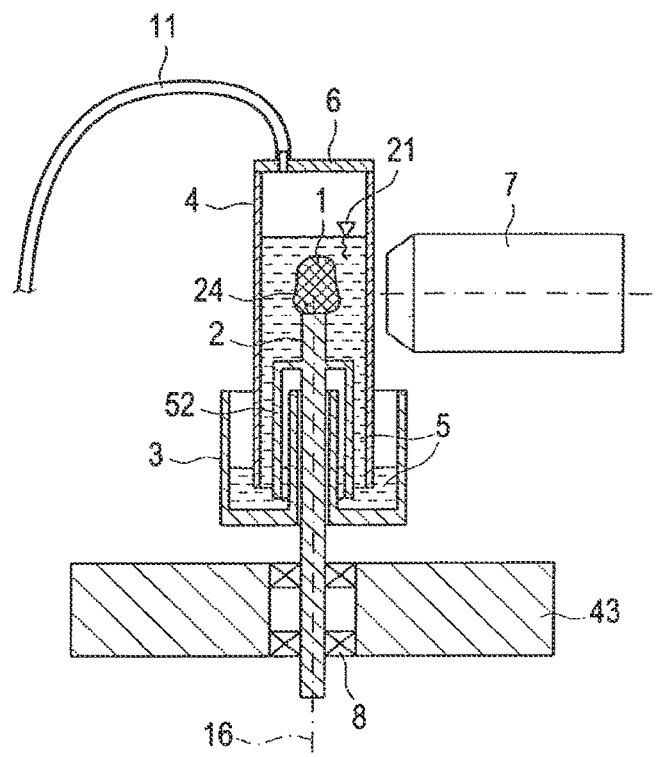
FIG. 10 shows an embodiment of the device with a ring-shaped bath.

FIG. 10 shows an embodiment of the device for examining samples in a liquid using a ring-shaped bath.

FIG. 10 shows a sample 1 which is fastened to the upper side 24 of a movable shaft 2. By way of example, the sample 1 can be fastened to the movable shaft 2 by adhesive bonding using an optically transparent adhesive. Further fastening options, such as e.g. clamping, are likewise conceivable. The shaft 2 is surrounded by a bath 3 which, in the embodiment depicted in FIG. 10, is opened toward the top and has a ring-shaped embodiment. The movable shaft 2 extends through the free region of the ring-shaped bath 3 and is not connected to the bath 3. A skirt 52 in the form of an upside-down beaker open toward the bottom, which reaches into the ring-shaped bath 3, is arranged at the movable shaft 2. The shaft 2 is held in a rotatable manner in a holder 43 by way of the bearing 8.

Before carrying out an optical examination on the sample 1, a cuvette 4 is placed over the shaft 2, for example as already explained in relation to the embodiment in FIG. 1. The fill level 21 of the immersion liquid 5 in the interior of the cuvette 4 is likewise set as explained in relation to e.g. FIG. 1.

For the purposes of carrying out the optical examination, an objective 7 is arranged outside of the cuvette 4, aligned horizontally with the sample 1, in the embodiment depicted in FIG. 10. Since the objective 7 is not coupled to the sample 1, it can be moved freely in relation to the latter. Depending on the examination process employed, it is also possible to arrange further optical components around the cuvette 4. The sample 1 can be rotated about the vertical axis 16, which in this case coincides with the axis of the shaft 2, during the examination by rotating the shaft 2 in the bearing 8.

Figure 11:
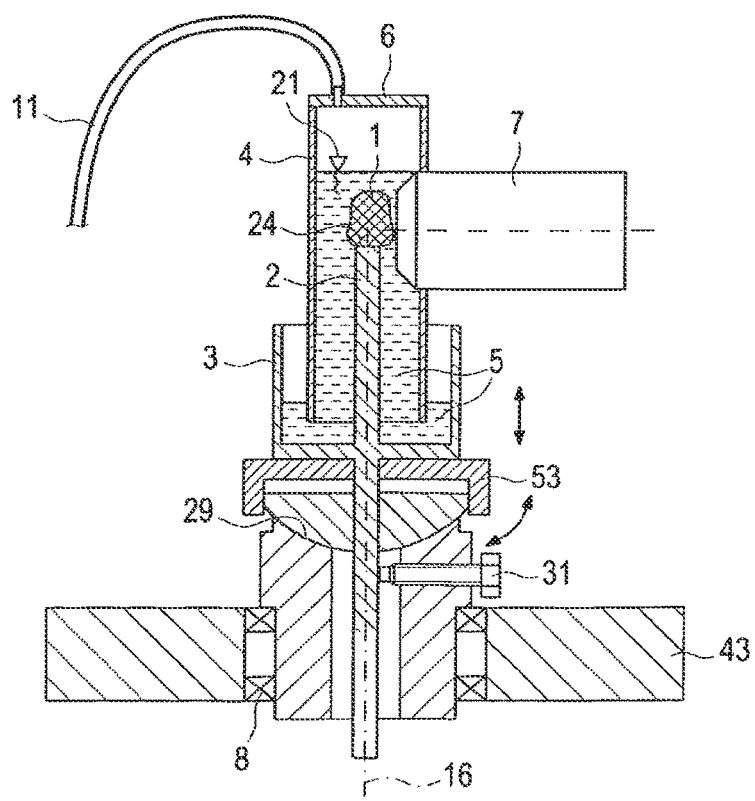
FIG. 11 shows an embodiment of the device with an inclinable and height-adjustable shaft.

FIG. 11 shows an embodiment of the device for examining samples in a liquid, with an inclinable and height-adjustable shaft.

FIG. 11 shows a sample 1 which is fastened to the upper side 24 of a movable shaft 2. By way of example, the sample 1 can be fastened to the movable shaft 2 by adhesive bonding using an optically transparent adhesive. Further fastening options, such as e.g. clamping, are likewise conceivable. The shaft 2 is surrounded by a bath 3 which, in the embodiment depicted in FIG. 11, is embodied as an upwardly open beaker and rigidly connected to the shaft 2. The shaft 2 and the bath 3 are arranged on a height-adjustment unit 53 such that the movable shaft 2 can be displaced vertically. In the depicted embodiment, the height-adjustment unit 53 comprises a female thread which engages in a male thread on a spherical support 29. By rotating the height-adjustment unit 53, it is possible to set the position thereof relative to the spherical support 29.

The spherical support 29 in turn is held in a rotatable manner in a bearing block 43 by way of the bearing 8.

In the depicted embodiment, the angle of inclination of the movable shaft 2 is set by an adjustment screw 31, which presses against the movable shaft 2. In further embodiments of the device, it is possible to arrange a further adjustment screw in order to enable an inclination of the movable shaft 2 in any direction.

Before carrying out an optical examination on the sample 1, a cuvette 4 is placed over the shaft 2, for example as already explained in relation to the embodiment in FIG. 1. The fill level 21 of the immersion liquid 5 in the interior of the cuvette 4 is likewise set as explained in relation to e.g. FIG. 1.

For the purposes of carrying out the optical examination, an objective 7 is let into the wall of the cuvette 4 and aligned horizontally onto the sample 1, like in the embodiment depicted in FIG. 2. The objective 7 is sealed in relation to the wall of the cuvette 4, for example by means of an elastomeric seal, or the objective 7 is adhesively bonded into the wall.

Figure 12:
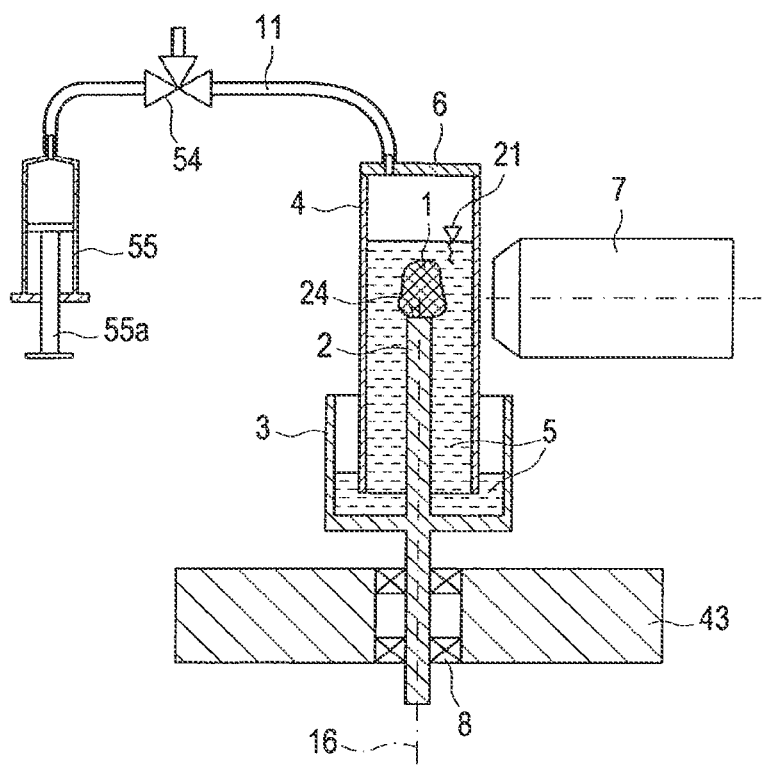
FIG. 12 shows a further embodiment of the device with a syringe.

FIG. 12 shows a further embodiment of the device for examining samples in a liquid, in which a syringe is used for generating a pressure difference.

FIG. 12 depicts a sample 1, which is fastened to the upper side 24 of a movable shaft 2. By way of example, the sample 1 can be fastened to the movable shaft 2 by adhesive bonding using an optically transparent adhesive. Further fastening options, such as e.g. clamping, are likewise conceivable. The shaft 2 is surrounded by a bath 3 which, in the embodiment depicted in FIG. 1, is embodied as an upwardly open beaker and rigidly connected to the shaft 2. The shaft 2 and the bath 3 are held in a rotatable manner in a holder 43 by way of the bearing 8.

Before carrying out an optical examination on the sample 1, a cuvette 4 is placed over the shaft 2 such that a gap remains between the lower side of the cuvette 4 and the base of the bath 3. The cuvette 3 has a cover 6, at which a tube 11 opens into the interior of the cuvette 4. The tube 11 is connected to a syringe 55 by way of a 3-way valve 54. The third connection of the 3-way valve is open.

In the situation depicted in FIG. 12, the bath 3 was filled with an immersion liquid 5 and the pressure within the cuvette 4 was subsequently reduced in relation to the pressure outside of the cuvette 4 by pulling back the plunger 55a of the syringe 55 such that the immersion liquid 5 is pressed into the interior of the cuvette 4 and completely surrounds the sample 1. While the cuvette 4 was being filled, the 3-way valve 54 was set in such a way that there was a continuous connection between the syringe 55 and the interior of the cuvette 4. After finishing the examination, the 3-way valve is switched such that the interior of the cuvette 4 is now connected to the open connector of the 3-way valve 54. Now air can stream into the interior of the cuvette 4 from the outside and the immersion liquid 5 flows back into the bath 3.

For the purposes of carrying out the optical examination, an objective 7 is arranged outside of the cuvette 4, aligned horizontally with the sample 1, in the embodiment depicted in FIG. 12. Since the objective 7 is not coupled to the sample 1, it can be moved freely in relation to the latter. Depending on the examination process employed, it is also possible to arrange further optical components around the cuvette 4. The sample 1 can be rotated about the vertical axis 16, which in this case coincides with the axis of the shaft 2, during the examination by rotating the shaft 2 in the bearing 8.

Figure 13:
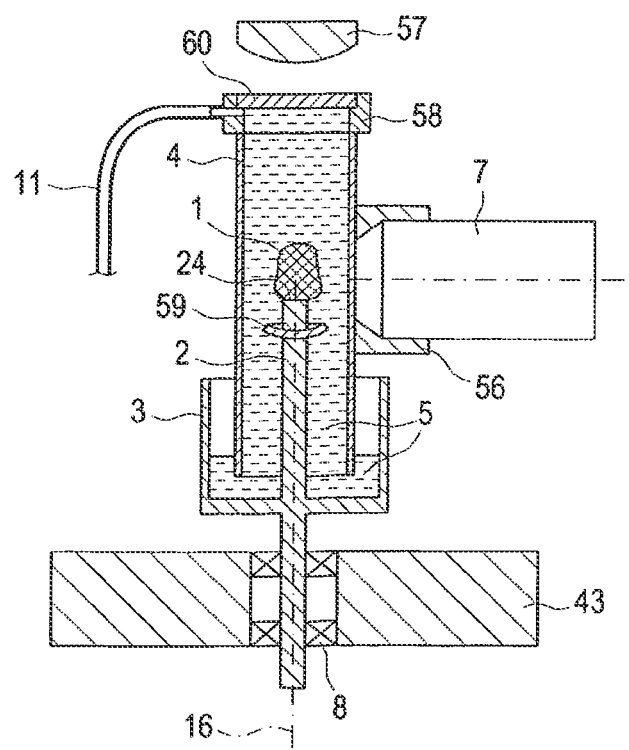
FIG. 13 shows an embodiment of the invention with an additional optical access from above.

FIG. 13 shows an embodiment of the device for examining samples in a liquid, with an additional optical access from above.

The device shown in FIG. 13 substantially corresponds to the arrangement already described in relation to FIG. 1; however, the embodiment depicted in FIG. 13 comprises additional optical components and the cuvette 4 has a cover 58 with an optical window 60 let therein. The connection for the tube 11 is embodied laterally in the cover 58 and opens into the interior directly below the window 60. The movable shaft 2 is embodied as an optical waveguide 17. A curved mirror 59 is arranged on the shaft 2 below the sample 1.

The interior of the cuvette 4 is connected to means for generating a pressure difference by way of the tube 11. In the situation depicted in FIG. 13, immersion liquid 5 was already pressed out of the bath 3 and into the interior of the cuvette 4 by way of a negative pressure such that said cuvette is completely filled.

An objective 7 is arranged on the right-hand side of the cuvette 4 by way of a holder 56 and it constitutes a horizontal optical access to the sample 1. The objective 7 can be optically coupled to the cuvette 4, e.g. by means of an air gap, by means of immersion liquid or by cementing. By way of example, the cuvette 4 can be displaced horizontally together with the objective 7 in order to position the objective 7 relative to the sample 1. Since the cuvette 4 is mechanically decoupled from the sample, it is also possible to move the sample 1 during an optical examination by way of moving the shaft 2. Vibrations that may occur in the process cannot be transmitted to the objective 7, and so an impairment of the measurement can be precluded.

The window 60 in the cover 58 constitutes a further optical access to the sample 1. Starting from the sample 1, light can be guided through the immersion liquid 5, which fills the interior of the cuvette 4, to the window 60. In the example depicted in FIG. 13, the light is collected by way of a converging lens 57 and fed to a detection unit. In order to increase the amount of light collected, the inner wall of the cuvette 4 is mirrored in those regions that do not adjoin the objective 7. Light emitted upward, but not directly in the direction of the window 60, by the sample can thus likewise reach the converging lens 57 by way of a reflection of the cuvette walls. Instead of partial mirroring of the cuvette walls, it is also possible to use total-internal reflection of the light at the outer walls of the cuvette 4. Light emitted downward can likewise be guided in the direction of the window 60 by way of the curved mirror 59, which is arranged on the movable shaft 2 below the sample 1.

Moreover, it is possible to guide the light emitted downward by the sample 1 to the outside by way of the movable shaft 2 configured as an optical waveguide 17 and to feed said light to detection optics. Optionally, collecting optics can be inserted between the sample 1 and the optical waveguide 17.

Figure 14:
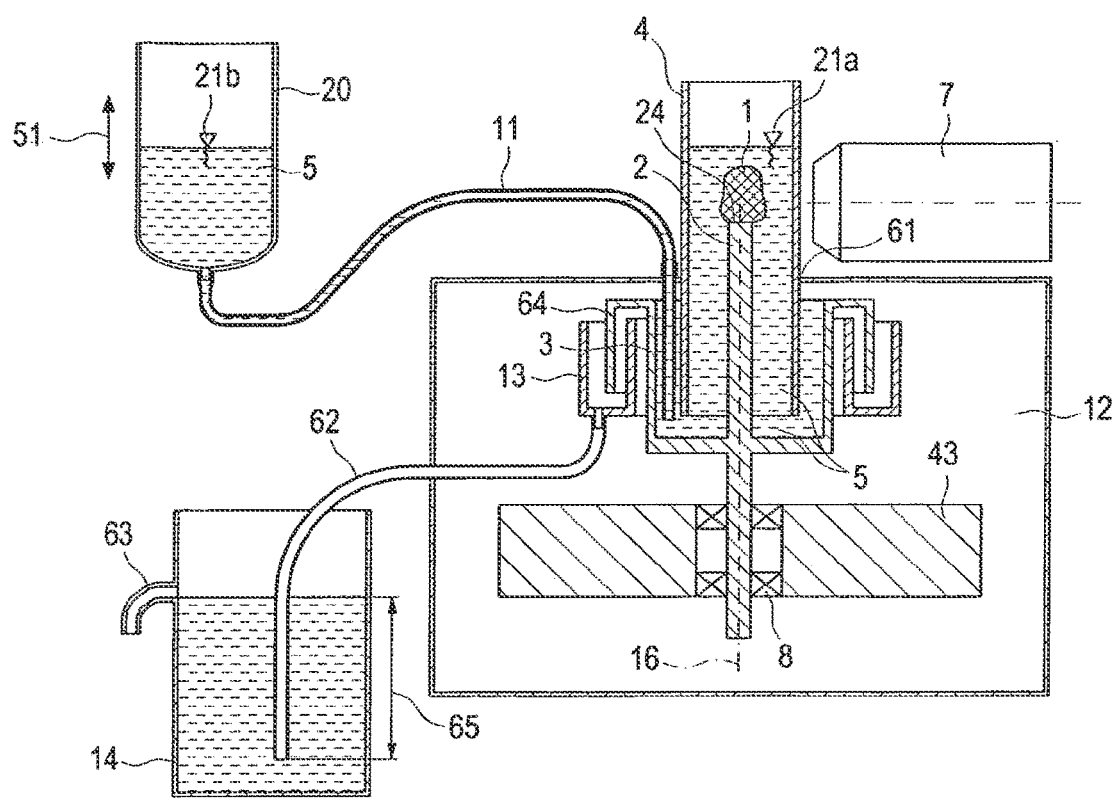
FIG. 14 shows a further embodiment of the device with a housing and a height-adjustable liquid reservoir.

FIG. 14 shows a further embodiment of the device for examining samples in a liquid, with a housing and a height-adjustable liquid reservoir.

The device depicted in FIG. 14 substantially corresponds to the embodiment in FIG. 5; however, a height-adjustable liquid reservoir 20 is used here as means for generating a pressure difference. The tube 11 connects the liquid reservoir 20 to the bath 3. On one side, the tube 11 opens into the liquid reservoir 20 at the lower side thereof. At the other end, the tube 11 opens into the bath 3, with the opening lying level with, or below, the lower edge of the cuvette 4. In this embodiment, both the liquid reservoir 20 and the cuvette 4 are configured open toward the top.

Before examining the sample, the reservoir 20, the cuvette 4 and the bath 3 are empty; the vessel 14 can already be filled so as to predetermine the maximum admissible fill level 21a of the liquid in the cuvette 4. Liquid 5 can be introduced into the device both by filling into the cuvette 4 and by filling into the height-adjustable liquid reservoir 20. Here, the liquid 5 initially flows into the bath 3. Air can escape from the interior of the housing 12 for as long as the fill level of the liquid 5 in the bath 3 has not yet reached the lower edge of the cuvette 4; there is no pressure increase in the region outside of the cuvette 4. Air is no longer able to escape from the housing 12 after the fill level has risen over the lower edge of the cuvette 4. The hydrostatic pressure in the liquid reservoir 20 and the hydrostatic pressure in the interior of the cuvette 4 are now connected by way of the tube 11 such that the hydrostatic pressure is equalized and the respective fill levels 21a and 21b are respectively equal. The hydrostatic pressure in the reservoir 20 can be modified by changing the height of the liquid reservoir 20, as a result of which it is also possible to influence the fill level 21a of the liquid 5 in the interior of the cuvette 4. If the reservoir 20 is lowered, the hydrostatic pressure in the liquid reservoir 20 is reduced. In order to compensate this, liquid 5 flows from the cuvette 4 into the reservoir 20 by way of the bath 3 and the tube 11 until the respective fill levels 21a and 21b, and hence the hydrostatic pressure, are equalized again. Conversely, it is possible to increase the fill level 21a in the interior of the cuvette 4 by lifting the reservoir 20.

As already described in relation to FIG. 5, the maximum fill level in this case is predetermined by the hydrostatic pressure of the liquid column 65 in the vessel 14. If the maximum predetermined fill level is exceeded, the fill level of the liquid 5 also starts to rise in the bath 3 outside of the cuvette 4, until said bath overflows and liquid reaches the overflow bath 3. The fill level 21a in the interior of the cuvette 4 cannot rise further and is therefore restricted.

The invention claimed is:

1. A device for positioning samples in a liquid,
comprising a movable shaft, to which the sample is fastened, and a cuvette, wherein the device comprises a bath, which surrounds the movable shaft, wherein the bath is fillable with the liquid,
the movable shaft is configured to receive the sample at the upper side thereof,
the movable shaft reaches into the cuvette from below, wherein said cuvette is open at least toward the bottom and configured to be immersed into the liquid in the bath with the underside thereof,
and, moreover, means are provided to generate a pressure difference between the interior of the cuvette and the region outside of the cuvette such that the fill level of the liquid in the cuvette is adjustable.

2. The device as claimed in claim 1, wherein the device is configured to carry out optical examinations of the sample.

3. The device as claimed in claim 1, wherein the device is configured to use an immersion liquid as liquid.

4. The device as claimed in claim 1, wherein the movable shaft is arranged in a rotatable manner.

5. The device as claimed in claim 1, wherein the bath is rigidly connected to the movable shaft.

6. The device as claimed in claim 1, wherein that the bath has a ring-shaped, circumferential, polygonal or square embodiment, wherein the bath encloses the movable shaft and wherein the movable shaft has the form of a beaker opened toward the bottom, which reaches into the bath.

7. The device as claimed in claim 1, wherein the means for generating the pressure difference are embodied as bellows, which are filled with a fluid and actuated by a force, as a syringe with a movable plunger, as a device for changing the volume of a space filled with a fluid, as a pump, as a height-adjustable liquid reservoir or as a combination of at least two of these means.

8. The device as claimed in claim 1, wherein means are arranged for restricting the pressure difference.

9. The device as claimed in claim 8, wherein the means for restricting the pressure difference are embodied as a liquid column with an overflow, as a pressure control valve, as an overflow or as a combination of at least two of these means.

10. The device as claimed in claim 1, wherein said device comprises a fill level regulation apparatus, which is configured to regulate the fill level of the liquid in the interior of the cuvette.

11. The device as claimed in claim 1, wherein the device comprises an optical access which is aligned horizontally.

12. The device as claimed in claim 11, wherein the optical access is embodied as an objective which is let into the wall of the cuvette and sealed in relation to the cuvette.

13. The device as claimed in claim 1, wherein the movable shaft is laterally displaceable, vertically displaceable and/or inclinable in relation to the vertical axis.

14. The device as claimed in claim 1, wherein the movable shaft is embodied as an optical waveguide or as a hollow shaft with an optical waveguide held in the interior.

15. The device as claimed in claim 1, wherein a lens is arranged at the upper side of the movable shaft.

16. The device as claimed in claim 1, wherein at least part of the wall of the cuvette is mirrored.

17. The device as claimed in claim 1, wherein at least parts of the cuvette are embodied as an optical waveguide.

18. The device as claimed in claim 1, wherein the bath is subdivided into two concentric regions, wherein the inner region is fillable with the liquid and the outer region is fillable with a liquid that is different to the liquid and wherein a cover is fastened to the cuvette, which cover covers the inner concentric region of the bath and which cover has an edge which reaches into the outer concentric region.

19. A method for examining samples in a liquid, comprising the following steps:
a) fixing the sample to the upper side of a movable shaft, wherein the shaft is surrounded by a bath,
b) positioning the sample in a cuvette that is open to the top or lowering a cuvette that is at least open toward the bottom over the shaft in the direction of the base of the bath, wherein a gap remains between the bath base and cuvette,
c) filling the bath with the liquid,
d) generating a pressure difference between the interior of the cuvette and the region outside of the cuvette, wherein the fill level of the liquid in the cuvette is set by setting the pressure difference,
e) carrying out the examination on the sample, wherein a relative movement between sample and cuvette is possible.

20. The method as claimed in claim 19, wherein the sample is moved during the optical examination in accordance with step e) by rotating the movable shaft about a vertical axis.

21. The method as claimed in claim 19, wherein, for the purposes of setting the pressure difference, the pressure within the cuvette is reduced in relation to the surroundings and/or the pressure in the region outside of the cuvette is increased in relation to the surrounding pressure.

22. The method as claimed in claim 19, wherein the fill level of the liquid is set with the aid of a controller.

23. The method as claimed in claim 19, wherein the sample is positioned by displacing and/or inclining the movable shaft in relation to a vertical axis.

24. The method as claimed in claim 19, wherein SLOT (scanning laser optical tomography), SPIM (single plane illumination microscopy), optical projection tomography (OPT), wide-field microscopy, transmission microscopy, confocal fluorescence microscopy, coherent anti-Stokes Raman scattering (CARS), nonlinear microscopy such as e.g. two or three photon microscopy or microscopy using high harmonics generation (HHG), confocal theta microscopy, fluorescence lifetime imaging microscopy (FLIM), stimulated emission detection microscopy (STED), structured illumination microscopy (SIM), localization microscopy (PALM/STORM), optical coherence tomography (OCT), x-ray microscopy, x-ray tomography, an imaging ultrasound method or digital holography is used for the examination.

25. A method for examining samples in a liquid, comprising the following steps:
a) fixing the sample to the upper side of a movable shaft, wherein the shaft is surrounded by a bath,
b) lowering a cuvette that is at least open toward the bottom over the shaft in the direction of the base of the bath, wherein a gap remains between the bath base and cuvette,
c) filling the bath with a first liquid which has a first density,
d) filling the bath with a second liquid with a second density, wherein the second density is less than the first density such that the weight of the second liquid with the second density acts on the first liquid and presses the latter into the cuvette,
e) carrying out the examination of the sample, wherein a relative movement between sample and cuvette is possible.

26. The method as claimed in claim 25 wherein SLOT (scanning laser optical tomography), SPIM (single plane illumination microscopy), optical projection tomography (OPT), wide-field microscopy, transmission microscopy, confocal fluorescence microscopy, coherent anti-Stokes Raman scattering (CARS), nonlinear microscopy such as e.g. two or three photon microscopy or microscopy using high harmonics generation (HHG), confocal theta microscopy, fluorescence lifetime imaging microscopy (FLIM), stimulated emission detection microscopy (STED), structured illumination microscopy (SIM), localization microscopy (PALM/STORM), optical coherence tomography (OCT), x-ray microscopy, x-ray tomography, an imaging ultrasound method or digital holography is used for the examination.

\* \* \* \* \*